United States Patent
Diev

(10) Patent No.: US 11,964,966 B2
(45) Date of Patent: Apr. 23, 2024

(54) POLYMERS FOR USE IN ELECTRONIC DEVICES

(71) Applicant: DUPONT ELECTRONICS, INC., Wilmington, DE (US)

(72) Inventor: Viacheslav V. Diev, Wilmington, DE (US)

(73) Assignee: DUPONT ELECTRONICS, INC., Wilmington, DE (US)

( * ) Notice: Subject to any disclaimer, the term of this patent is extended or adjusted under 35 U.S.C. 154(b) by 751 days.

(21) Appl. No.: 17/265,916

(22) PCT Filed: Aug. 7, 2019

(86) PCT No.: PCT/US2019/045410
§ 371 (c)(1),
(2) Date: Feb. 4, 2021

(87) PCT Pub. No.: WO2020/033480
PCT Pub. Date: Feb. 13, 2020

(65) Prior Publication Data
US 2021/0198243 A1      Jul. 1, 2021

Related U.S. Application Data

(60) Provisional application No. 62/715,904, filed on Aug. 8, 2018.

(51) Int. Cl.
*C07D 405/14*       (2006.01)
*C07D 405/00*       (2006.01)
(Continued)

(52) U.S. Cl.
CPC ......... *C07D 405/14* (2013.01); *C07D 405/00* (2013.01); *C07D 491/18* (2013.01); *C08G 69/26* (2013.01); *C08G 73/1085* (2013.01)

(58) Field of Classification Search
CPC ... C07D 405/00; C07D 405/14; C07D 491/18
See application file for complete search history.

(56) References Cited

U.S. PATENT DOCUMENTS 5,166,308 A    11/1992   Kreuz et al.
5,298,331 A     3/1994   Kanakarajan et al.
(Continued)

FOREIGN PATENT DOCUMENTS

CN     101481378 A     7/2009
CN     104448311 A     3/2015
(Continued)

OTHER PUBLICATIONS

CRC Handbook of Chemistry and Physics, 81st Edition (2000-2001).
(Continued)

*Primary Examiner* — Marc S Zimmer
*Assistant Examiner* — Surbhi M Du
(74) *Attorney, Agent, or Firm* — G. Creston Campbell

(57) ABSTRACT

Disclosed is a polyanhydride having Formula I

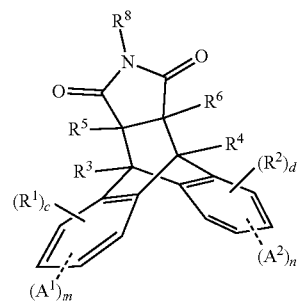

where A is
In Formula I: $R^1$ and $R^2$ are the same or different at each occurrence and are F, CN, alkyl, fluoroalkyl, alkoxy, fluoroalkoxy, silyl, siloxy, unsubstituted or substituted hydrocarbon aryl, unsubstituted or substituted heteroaryl, or unsubstituted or substituted aryloxy; $R^3$ and $R^4$ are the same or different and are $A^3$, $A^4$, H, F, CN, alkyl, fluoroalkyl, alkoxy, fluoroalkoxy, silyl, siloxy, unsubstituted or substi-
(Continued)

tuted hydrocarbon aryl, unsubstituted or substituted heteroaryl, or unsubstituted or substituted aryloxy; $R^5$ and $R^6$ are the same or different and are H, F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy; $R^8$ is selected from the group consisting of alkyl, silyl, unsubstituted or substituted hydrocarbon aryl, or unsubstituted or substituted heteroaryl; c and d are the same or different and are an integer from 0 to the maximum available; m and n are the same or different and are 0 or 1; $A^1$ to $A^4$ are the same or different and have the formula

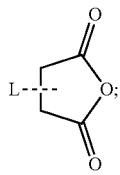

single dashed lines between two rings indicate that the rings are joined by a single bond or fused together at any available position; L is a bond or a hydrocarbon aryl; and at least two A groups are present.

10 Claims, 2 Drawing Sheets

(51) Int. Cl.
*C07D 491/18* (2006.01)
*C08G 69/26* (2006.01)
*C08G 73/10* (2006.01)

(56) References Cited

U.S. PATENT DOCUMENTS

| 6,153,064 | A | 11/2000 | Condra et al. |
| 9,840,514 | B2 | 12/2017 | Ma et al. |
| 2004/0102577 | A1 | 5/2004 | Hsu et al. |
| 2004/0127637 | A1 | 7/2004 | Hsu et al. |
| 2005/0184287 | A1 | 8/2005 | Herron et al. |
| 2005/0205860 | A1 | 9/2005 | Hsu et al. |

FOREIGN PATENT DOCUMENTS

| CN | 105037383 A | 11/2015 |
| CN | 106139936 A | 11/2016 |
| CN | 107488261 A | 12/2017 |
| WO | 2005/052027 A1 | 6/2005 |
| WO | 2007/145979 A2 | 12/2007 |
| WO | 2016/153064 A1 | 1/2018 |
| WO | 2018/062425 A1 | 8/2019 |

OTHER PUBLICATIONS

Gustafsson et al., "Flexible light-emitting diodes made from soluble conducting polymer," Nature vol. 357, pp. 477 479 (Jun. 11, 1992).
Y. Wang, Kirk-Othmer Encyclopedia of Chemical Technology, Fourth Edition, vol. 18, pp. 837-860 (1996).
Xiao, Y. et al., "Microporous aromatic polyimides derived from triptycene-based dianhydride", Chinese Chemical Letters, 2016, vol. 27, pp. 454-458.
Rafiee, Z. "Ultra-rapid polyamidation reaction of optically active aromatic diacid containing methionine moieties with aromatic diamines under microwave irradiation", Journal of Polymer Research, 2015, vol. 22, pp. 1-10.
PCT International Search Report for Application No. PCT/US2019/045410; Park, Je Hyun, Authorized Officer; ISA/KR; dated Nov. 25, 2019.

POLYMERS FOR USE IN ELECTRONIC DEVICES

CLAIM OF BENEFIT OF PRIOR APPLICATION

This application claims the benefit of U.S. Provisional Application No. 62/715,904, filed Aug. 8, 2018, which is incorporated in its entirety herein by reference.

BACKGROUND INFORMATION

Field of the Disclosure

The present disclosure relates to novel polymeric compounds. The disclosure further relates to methods for preparing such polymeric compounds and electronic devices having at least one layer comprising these materials.

Description of the Related Art

Materials for use in electronics applications often have strict requirements in terms of their structural, optical, thermal, electronic, and other properties. As the number of commercial electronics applications continues to increase, the breadth and specificity of requisite properties demand the innovation of materials with new and/or improved properties. Polyimides represent a class of polymeric compounds that has been widely used in a variety of electronics applications. They can serve as a flexible replacement for glass in electronic display devices provided that they have suitable properties. These materials can function as a component of Liquid Crystal Displays ("LCDs"), where their modest consumption of electrical power, light weight, and layer flatness are critical properties for effective utility. Other uses in electronic display devices that place such parameters at a premium include device substrates, substrates for color filter sheets, cover films, touch screen panels, and others.

A number of these components are also important in the construction and operation of organic electronic devices having an organic light emitting diode ("OLED"). OLEDs are promising for many display applications because of their high power conversion efficiency and applicability to a wide range of end-uses. They are increasingly being used in cell phones, tablet devices, handheld/laptop computers, and other commercial products. These applications call for displays with high information content, full color, and fast video rate response time in addition to low power consumption.

Polyimide films generally possess sufficient thermal stability, high glass transition temperature, and mechanical toughness to merit consideration for such uses. Also, polyimides generally do not develop haze when subject to repeated flexing, so they are often preferred over other transparent substrates like polyethylene terephthalate (PET) and polyethylene naphthalate (PEN) in flexible display applications. Polyimide films generally possess sufficient thermal stability, high glass transition temperature, and mechanical toughness to merit consideration for such uses. Also, polyimides generally do not develop haze when subject to repeated flexing, so they are often preferred over other transparent substrates like polyethylene terephthalate (PET) and polyethylene naphthalate (PEN) in flexible display applications.

Polyimides are generally stiff, highly aromatic materials; and the polymer chains tend to orient in the plane of the film/coating as the film/coating is being formed. This leads to differences in refractive index in the parallel vs. perpendicular directions of the film (birefringence) which produces optical retardation that can negatively impact display performance. New monomers with novel structural features can potentially lead to polyimides with improved properties for specific applications.

There is a continuing need for polymer materials that are suitable for use in electronic devices.

SUMMARY

There is provided a polyanhydride having Formula I

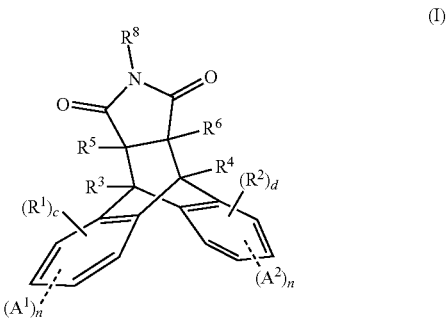

wherein:
- $R^1$ and $R^2$ are the same or different at each occurrence and are selected from the group consisting of F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy;
- $R^3$ is selected from the group consisting of $A^3$, H, F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy;
- $R^4$ is selected from the group consisting of $A^4$, H, F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy;
- $R^5$ and $R^6$ are the same or different and are selected from the group consisting of H, F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy;
- $R^8$ is selected from the group consisting of alkyl, silyl, unsubstituted or substituted hydrocarbon aryl, and unsubstituted or substituted heteroaryl;
- c and d are the same or different and are an integer from 0 to the maximum available;
- m and n are the same or different and are 0 or 1;
- $A^1$ to $A^4$ are the same or different and have the formula

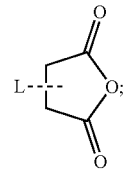

L is the same or different at each occurrence and is a bond or a hydrocarbon aryl; and single dashed lines between two rings indicate that the rings are joined by a single bond or fused together at any available position;

with the proviso that at least two of $A^1$ to $A^4$ are present.

There is further provided a polyamic acid having a repeat unit of Formula II

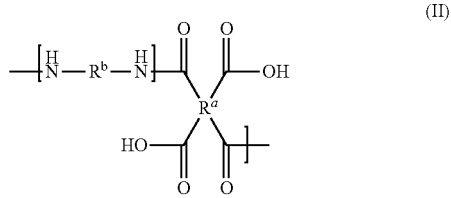
(II)

where:

$R^a$ is the same or different at each occurrence and represents one or more tetracarboxylic acid component residues; and $R^b$ is the same or different at each occurrence and represents one or more aromatic diamine residues;

wherein 10-100 mol % of $R^a$ is a dianhydride residue from one or more dianhydrides having Formula I.

There is further provided a composition comprising (a) the polyamic acid having a repeat unit of Formula II and (b) a high-boiling, aprotic solvent.

There is further provided a polyimide whose repeat units have the structure in Formula III

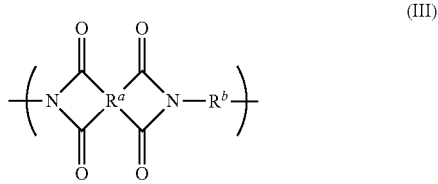
(III)

where $R^a$ and $R^b$ are as defined in Formula II.

There is further provided a polyimide film comprising a polyimide having the repeat unit of Formula III.

There is further provided one or more methods for preparing a polyimide film wherein the polyimide has the repeat unit of Formula III.

There is further provided a flexible replacement for glass in an electronic device wherein the flexible replacement for glass is a polyimide film comprising a polyimide having the repeat unit of Formula III.

There is further provided an electronic device having at least one layer comprising a polyimide film comprising a polyimide having the repeat unit of Formula III.

There is further provided an organic electronic device, such as an OLED, wherein the organic electronic device contains a flexible replacement for glass as disclosed herein.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
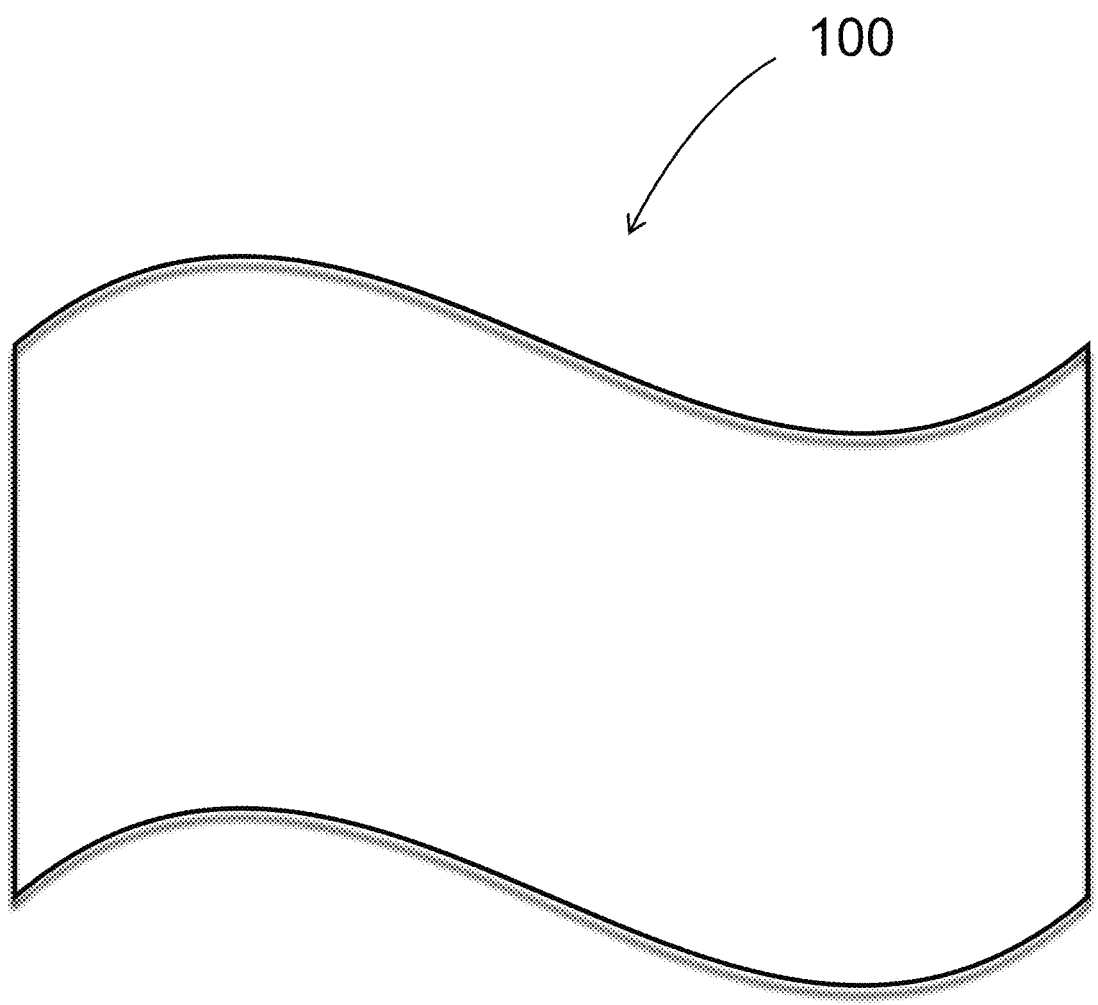
FIG. 1 includes an illustration of one example of a polyimide film that can act as a flexible replacement for glass.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

There is provided a polyanhydride having Formula I, as described in detail below.

There is further provided a polyamic acid having repeat units of Formula II, as described in detail below.

There is further provided a composition comprising (a) the polyamic acid having repeat units of Formula II and (b) a high-boiling, aprotic solvent.

There is further provided a polyimide whose repeat units have the structure in Formula III, as described in detail below.

There is further provided one or more methods for preparing a polyimide film wherein the polyimide has the repeat unit of Formula III.

There is further provided a flexible replacement for glass in an electronic device wherein the flexible replacement for glass is a polyimide film comprising a polyimide having the repeat unit of Formula III.

There is further provided an electronic device having at least one layer comprising a polyimide film comprising a polyimide having the repeat unit of Formula III.

There is further provided an organic electronic device, such as an OLED, wherein the organic electronic device contains a flexible replacement for glass as disclosed herein.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms, followed by the Polyanhydride Having Formula I, the Polyamic Acid, the Polyimide, the Methods for Preparing Polyimide Films, the Electronic Device, and finally Examples.

1. Definitions and Clarification of Terms

Before addressing details of embodiments described below, some terms are defined or clarified.

As used in the "Definitions and Clarification of Terms", R, $R^a$, $R^b$, R', R" and any other variables are generic designations and may be the same as or different from those defined in the formulas.

The term "alignment layer" is intended to mean a layer of organic polymer in a liquid-crystal device (LCD) that aligns the molecules closest to each plate as a result of its being rubbed onto the LCD glass in one preferential direction during the LCD manufacturing process.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tert-butyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aprotic" refers to a class of solvents that lack an acidic hydrogen atom and are therefore incapable of acting as hydrogen donors. Common aprotic solvents include alkanes, carbon tetrachloride (CCl4), benzene, dimethyl formamide (DMF), N-methyl-2-Pyrrolidone (NMP), dimethylacetamide (DMAc), and many others.

The term "aromatic compound" is intended to mean an organic compound comprising at least one unsaturated cyclic group having 4n+2 delocalized pi electrons. The term is intended to encompass both aromatic compounds having only carbon and hydrogen atoms, and heteroaromatic compounds wherein one or more of the carbon atoms within the cyclic group has been replaced by another atom, such as nitrogen, oxygen, sulfur, or the like.

The term "aryl" or "aryl group" a moiety formed by removal of one or more hydrogen ("H") or deuterium ("D") from an aromatic compound. The aryl group may be a single ring (monocyclic) or have multiple rings (bicyclic, or more) fused together or linked covalently. A "hydrocarbon aryl" has only carbon atoms in the aromatic ring(s). A "heteroaryl" has one or more heteroatoms in at least one aromatic ring. In some embodiments, hydrocarbon aryl groups have 6 to 60 ring carbon atoms; in some embodiments, 6 to 30 ring carbon atoms. In some embodiments, heteroaryl groups have from 4-50 ring carbon atoms; in some embodiments, 4-30 ring carbon atoms.

The term "alkoxy" is intended to mean the group —OR, where R is alkyl.

The term "aryloxy" is intended to mean the group —OR, where R is aryl.

Unless otherwise indicated, all groups can be substituted or unsubstituted. An optionally substituted group, such as, but not limited to, alkyl or aryl, may be substituted with one or more substituents which may be the same or different. Suitable substituents include alkyl, aryl, nitro, cyano, —N(R')(R"), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxy, siloxane, thioalkoxy, —S(O)$_2$—, —C(=O)—N(R')(R"), (R')(R")N-alkyl, (R')(R")N-alkoxyalkyl, (R')(R") N-alkylaryloxyalkyl, —S(O)$_s$-aryl (where s=0-2) or —S(O)$_s$-heteroaryl (where s=0-2). Each R' and R" is independently an optionally substituted alkyl, cycloalkyl, or aryl group. R' and R", together with the nitrogen atom to which they are bound, can form a ring system in certain embodiments. Substituents may also be crosslinking groups.

The term "amine" is intended to mean a compound that contains a basic nitrogen atom with a lone pair, where "lone pair" refers to a set of two valence electrons that are not shared with another atom. The term "amino" refers to the functional group —NH$_2$, —NHR, or —NR$_2$, where R is the same or different at each occurrence and can be an alkyl group or an aryl group. The term "diamine" is intended to mean a compound that contains two basic nitrogen atoms with associated lone pairs. The term "polyamine" is intended to mean a compound that contains two or more basic nitrogen atoms with associated lone pairs. The term "aromatic diamine" is intended to mean an aromatic compound having two amino groups. The term "aromatic polyamine" is intended to mean an aromatic compound having two or more amino groups. The term "bent diamine" is intended to mean a diamine wherein the two basic nitrogen atoms and associated lone pairs are asymmetrically disposed about the center of symmetry of the corresponding compound or functional group, e.g. m-phenylenediamine:

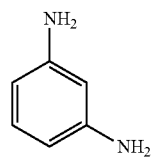

The term "aromatic diamine residue" is intended to mean the moiety bonded to the two amino groups in an aromatic diamine. The term "aromatic diisocyanate residue" is intended to mean the moiety bonded to the two isocyanate groups in an aromatic diisocyanate compound. This is further illustrated below.

Polyamine/Polyisocyanate Residue

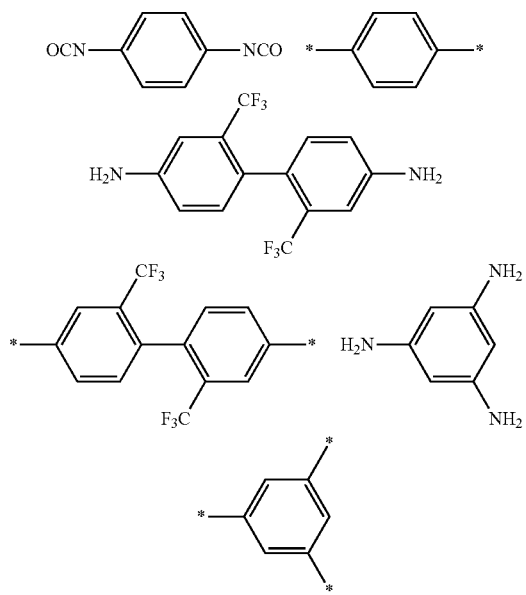

The terms "diamine residue" and "diisocyanate residue" are intended to mean the moiety bonded to two amino groups or two isocyanate groups, respectively, where the moiety is aliphatic or aromatic. The terms "polyamine residue" and "polyisocyanate residue" are intended to mean the moiety bonded to two or more amino groups or two or more isocyanate groups, respectively, where the moiety is aliphatic or aromatic.

The term "b*" is intended to mean the b* axis in the CIELab Color Space that represents the yellow/blue opponent colors. Yellow is represented by positive b* values, and blue is represented by negative b* values. Measured b* values may be affected by solvent, particularly since solvent choice may affect color measured on materials exposed to high-temperature processing conditions. This may arise as the result of inherent properties of the solvent and/or properties associated with low levels of impurities contained in various solvents. Particular solvents are often preselected to achieve desired b* values for a particular application.

The term "birefringence" is intended to mean the difference in the refractive index in different directions in a polymer film or coating. This term usually refers to the difference between the x- or y-axis (in-plane) and the z-axis (out-of-plane) refractive indices.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "linear coefficient of thermal expansion (CTE or a)" is intended to mean the parameter that defines the amount which a material expands or contracts as a function of temperature. It is expressed as the change in length per degree Celsius and is generally expressed in units of $\mu m/m/°C$ or $ppm/°C$.

$$a=(\Delta L/L_0)/\Delta T$$

Measured CTE values disclosed herein are made via known methods during the first or second heating scan. The understanding of the relative expansion/contraction characteristics of materials can be an important consideration in the fabrication and/or reliability of electronic devices.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" as it refers to a layer or a material, is intended to indicate a layer or material which electronically facilitates the operation of the device. Examples of electroactive materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The term "tensile elongation" or "tensile strain" is intended to mean the percentage increase in length that occurs in a material before it breaks under an applied tensile stress. It can be measured, for example, by ASTM Method D882.

The prefix "fluoro" is intended to indicate that one or more hydrogens in a group have been replaced with fluorine.

The term "glass transition temperature (or $T_g$)" is intended to mean the temperature at which a reversible change occurs in an amorphous polymer or in amorphous regions of a semi crystalline polymer where the material changes suddenly from a hard, glassy, or brittle state to one that is flexible or elastomeric. Microscopically, the glass transition occurs when normally-coiled, motionless polymer chains become free to rotate and can move past each other. $T_g$'s may be measured using differential scanning calorimetry (DSC), thermo-mechanical analysis (TMA), or dynamic-mechanical analysis (DMA), or other methods.

The prefix "hetero" indicates that one or more carbon atoms have been replaced with a different atom. In some embodiments, the heteroatom is O, N, S, or combinations thereof.

The term "high-boiling" is intended to indicate a boiling point greater than 130° C.

The term "host material" is intended to mean a material to which a dopant is added. The host material may or may not have electronic characteristic(s) or the ability to emit, receive, or filter radiation. In some embodiments, the host material is present in higher concentration.

The term "isothermal weight loss" is intended to mean a material's property that is directly related to its thermal stability. It is generally measured at a constant temperature of interest via thermogravimetric analysis (TGA). Materials that have high thermal stability generally exhibit very low percentages of isothermal weight loss at the required use or processing temperature for the desired period of time and can therefore be used in applications at these temperatures without significant loss of strength, outgassing, and/or change in structure.

The term "laser particle counter test" refers to a method used to assess the particle content of polyamic acid and other polymeric solutions whereby a representative sample of a test solution is spin coated onto a 5" silicon wafer and soft baked/dried. The film thus prepared is evaluated for particle content by any number of standard measurement techniques. Such techniques include laser particle detection and others known in the art.

The term "liquid composition" is intended to mean a liquid medium in which a material is dissolved to form a solution, a liquid medium in which a material is dispersed to form a dispersion, or a liquid medium in which a material is suspended to form a suspension or an emulsion.

The term "matrix" is intended to mean a foundation on which one or more layers is deposited in the formation of, for example, an electronic device. Non-limiting examples include glass, silicon, and others.

The term "1% TGA Weight Loss" is intended to mean the temperature at which 1% of the original polymer weight is lost due to decomposition (excluding absorbed water).

The term "optical retardation (or $R_{TH}$)" is intended to mean the difference between the average in-plane refractive index and the out-of-plane refractive index (i.e., the birefringence), this difference then being multiplied by the thickness of the film or coating. Optical retardation is typically measured for a given frequency of light, and the units are reported in nanometers.

The term "organic electronic device" or sometimes "electronic device" is herein intended to mean a device including one or more organic semiconductor layers or materials.

The term "particle content" is intended to mean the number or count of insoluble particles that is present in a solution. Measurements of particle content can be made on the solutions themselves or on finished materials (pieces, films, etc.) prepared from those films. A variety of optical methods can be used to assess this property.

The term "photoactive" refers to a material or layer that emits light when activated by an applied voltage (such as in a light emitting diode or chemical cell), that emits light after the absorption of photons (such as in down-converting phosphor devices), or that responds to radiant energy and generates a signal with or without an applied bias voltage (such as in a photodetector or a photovoltaic cell).

The term "polyamic acid solution" refers to a solution of a polymer containing amic acid units that have the capability of intramolecular cyclization to form imide groups.

The term "polyanhydride" refers to a compound having two or more acid anhydride groups. The term "polyanhydride residue" is intended to mean the moiety bonded to the two or more anhydride groups. This is further illustrated below.

Polyanhydride Residue

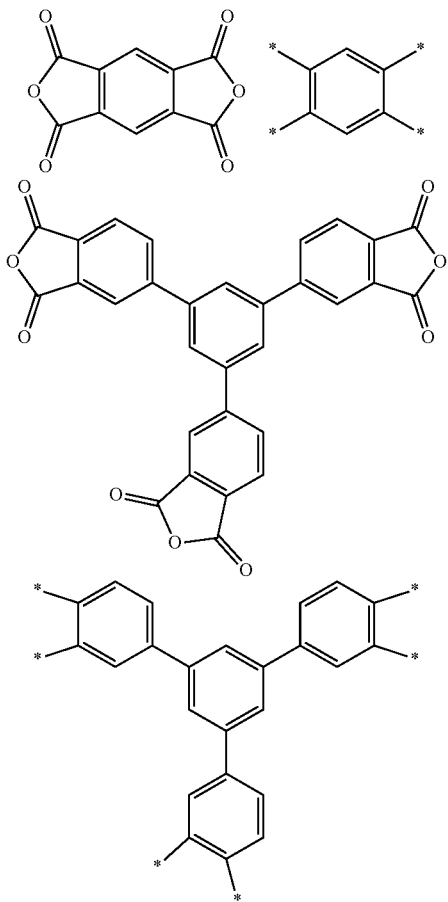

The term "polyimide" refers to condensation polymers resulting from the reaction of one or more polyfunctional carboxylic acid components with one or more primary polyamines or polyisocyanates. They contain the imide structure —CO—NR—CO— as a linear or heterocyclic unit along the main chain of the polymer backbone. In some embodiments, the polyimide results from the reaction of one or more bifunctional carboxylic acid components with one or more primary diamines or diisocyanates.

The term "satisfactory," when regarding a materials property or characteristic, is intended to mean that the property or characteristic fulfills all requirements/demands for the material in-use. For example, an isothermal weight loss of less than 1% at 350° C. for 3 hours in nitrogen can be viewed as a non-limiting example of a "satisfactory" property in the context of the polyimide films disclosed herein.

The term "soft-baking" is intended to mean a process commonly used in electronics manufacture wherein coated materials are heated to drive off solvents and solidify a film. Soft-baking is commonly performed on a hot plate or in exhausted oven at temperatures between 90° C. and 110° C. as a preparation step for subsequent thermal treatment of coated layers or films.

The term "substrate" refers to a base material that can be either rigid or flexible and may include one or more layers of one or more materials, which can include, but are not limited to, glass, polymer, metal or ceramic materials or combinations thereof. The substrate may or may not include electronic components, circuits, or conductive members.

The term "siloxane" refers to the group $R_3SiOR_2Si—$, where R is the same or different at each occurrence and is H, C1-20 alkyl, fluoroalkyl, or aryl. In some embodiments, one or more carbons in an R alkyl group are replaced with Si.

The term "siloxy" refers to the group $R_3SiO—$, where R is the same or different at each occurrence and is H, C1-20 alkyl, fluoroalkyl, or aryl.

The term "silyl" refers to the group $R_3Si—$, where R is the same or different at each occurrence and is H, C1-20 alkyl, fluoroalkyl, or aryl. In some embodiments, one or more carbons in an R alkyl group are replaced with Si.

The term "spin coating" is intended to mean a process used to deposit uniform thin films onto flat substrates. Generally, a small amount of coating material is applied on the center of the substrate, which is either spinning at low speed or not spinning at all. The substrate is then rotated at specified speeds in order to spread the coating material uniformly by centrifugal force.

The term "spiro group" refers to a group having a bicyclic organic portion where the two rings have a single atom in common. The rings can be different in nature or identical, and may form part of other ring systems. The common atom has two bonds in each ring and is called the spiroatom. In some embodiments, the spiroatom is selected from the group consisting of C and Si.

The term "tensile modulus" is intended to mean the measure of the stiffness of a solid material that defines the initial relationship between the stress (force per unit area) and the strain (proportional deformation) in a material like a film. Commonly used units are giga pascals (GPa).

The term "tetracarboxylic acid component" is intended to mean any one or more of the following: a tetracarboxylic acid, a tetracarboxylic acid monoanhydride, a tetracarboxylic acid dianhydride, a tetracarboxylic acid monoester, and a tetracarboxylic acid diester.

The term "tetracarboxylic acid component residue" is intended to mean the moiety bonded to the four carboxy groups in a tetracarboxylic acid component. This is further illustrated below.

Tetracarboxylic acid component Residue

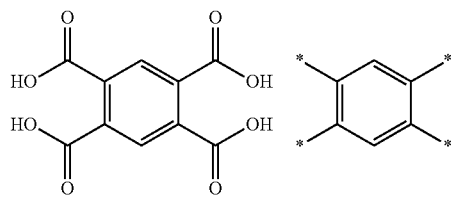

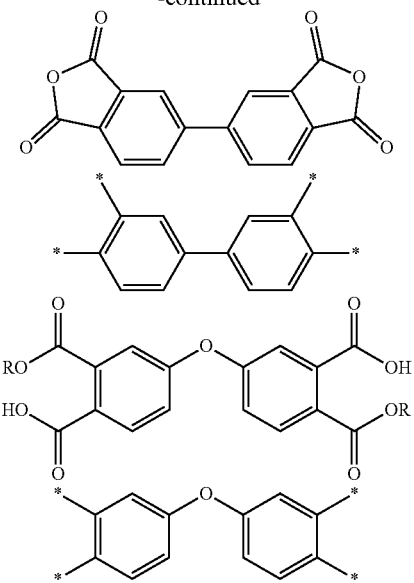

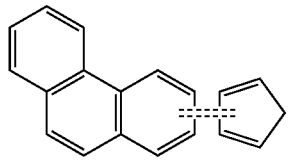

Formula i could have the structure shown as i-1, i-2, or i-3.

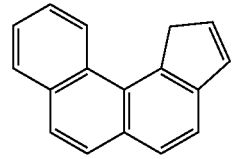

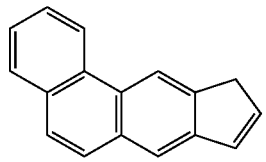

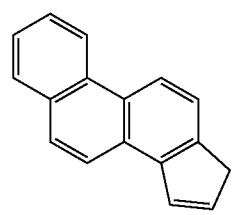

The term "transmittance" refers to the percentage of light of a given wavelength impinging on a film that passes through the film so as to be detectable on the other side. Light transmittance measurements in the visible region (380 nm to 800 nm) are particularly useful for characterizing film-color characteristics that are most important for understanding the properties-in-use of the polyimide films disclosed herein.

The term "yellowness index (or YI)" refers to the magnitude of yellowness relative to a standard. A positive value of YI indicates the presence, and magnitude, of a yellow color. Materials with a negative YI appear bluish. It should also be noted, particularly for polymerization and/or curing processes run at high temperatures, that YI can be solvent dependent. The magnitude of color introduced using DMAC as a solvent, for example, may be different than that introduced using NMP as a solvent. This may arise as the result of inherent properties of the solvent and/or properties associated with low levels of impurities contained in various solvents. Particular solvents are often preselected to achieve desired YI values for a particular application.

In a structure where a substituent bond passes through one or more rings as shown below,

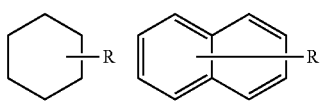

it is meant that the substituent R may be bonded at any available position on the one or more rings.

In a structure, different types of bonds are indicated as shown below:
—(solid line) indicates a single bond
=(solid double lines) indicates a double bond
------(single dashed line) indicates a single bond or a fused bond
======(double dashed lines) indicates a fused bond, where two rings are fused together in any available position. As an illustration of a fused bond, the formula i is shown below The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). Exemplary adjacent R groups are shown below:

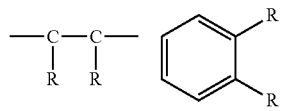

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the CRC Handbook of Chemistry and Physics, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Polyanhydride Having Formula I

The polyanhydride described herein has Formula I

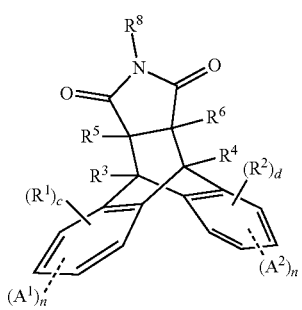

(I)

wherein:
$R^1$ and $R^2$ are the same or different at each occurrence and are selected from the group consisting of F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy;

$R^3$ is selected from the group consisting of $A^3$, H, F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy;

$R^4$ is selected from the group consisting of $A^4$, H, F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy;

$R^5$ and $R^6$ are the same or different and are selected from the group consisting of H, F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy;

$R^8$ is selected from the group consisting of alkyl, silyl, unsubstituted or substituted hydrocarbon aryl, and unsubstituted or substituted heteroaryl;

c and d are the same or different and are an integer from 0 to the maximum available;

m and n are the same or different and are 0 or 1;

$A^1$ to $A^4$ are the same or different and have the formula

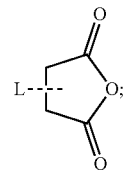

L is the same or different at each occurrence and is a bond or a hydrocarbon aryl; and single dashed lines between two rings indicate that the rings are joined by a single bond or fused together at any available position;

with the proviso that at least two of $A^1$ to $A^4$ are present.

In some embodiments of Formula I, exactly two of $A^1$ to $A^4$ are present and the compound is a dianhydride.

In some embodiments of Formula I, exactly three of $A^1$ to $A^4$ are present and the compound is a trianhydride.

In some embodiments of Formula I, all of $A^1$ to $A^4$ are present and the compound is a tetraanhydride.

In some embodiments of Formula I, m=0.

In some embodiments of Formula I, m=1.

In some embodiments of Formula I, n=0.

In some embodiments of Formula I, n=1.

In some embodiments of Formula I, m=n=1, $R^3 \neq A^3$, and $R^4 \neq A^4$.

In some embodiments of Formula I, m=n=0, $R^3 = A^3$, and $R^4 = A^4$.

In some embodiments of Formula I, L is a bond.

In some embodiments of Formula I, L is an unsubstituted or substituted $C_{6-30}$ hydrocarbon aryl; in some embodiments, an unsubstituted or substituted $C_{6-18}$ hydrocarbon aryl; in some embodiments, an unsubstituted or substituted $C_{6-12}$ hydrocarbon aryl; in some embodiments, unsubstituted. The substituted hydrocarbon aryl group may have one or more substitutents selected from the group consisting of F, CN, alkyl, fluoroalkyl, alkoxy, fluoroalkoxy, silyl, and siloxy.

In some embodiments of Formula I, —L— represents a single bond.

In some embodiments of Formula I, —L— represents a fused bond.

In some embodiments of Formula I, —L— represents a structure selected from the group consisting of

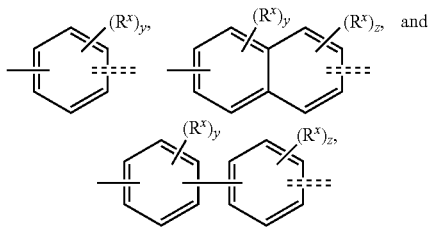

wherein:
R$^x$ is the same or different at each occurrence and is selected from the group consisting of F, CN, alkyl, fluoroalkyl, alkoxy, fluoroalkoxy, silyl, and siloxy;
y and z are the same or different and are an integer from 0 to the maximum available; and
double dashed lines between two rings indicate that the rings are fused in any available position.

In some embodiments of the above formulas, y=z=0.
In some embodiments of the above formulas, y=0.
In some embodiments of the above formulas, y=1.
In some embodiments of the above formulas, y=2.
In some embodiments of the above formulas, y=3.
In some embodiments of the above formulas, y=4.
In some embodiments of the above formulas, y>0.
In some embodiments of the above formulas, z=0.
In some embodiments of the above formulas, z=1.
In some embodiments of the above formulas, z=2.
In some embodiments of the above formulas, z=3.
In some embodiments of the above formulas, z>0.
In some embodiments of the above formulas, y>0 and at least one R$^x$ is F.
In some embodiments of the above formulas, y>0 and at least one R$^x$ is a $C_{1-20}$ alkyl; in some embodiments $C_{1-10}$ alkyl; in some embodiments, methyl.
In some embodiments of the above formulas, y>0 and at least one R$^x$ is a $C_{1-20}$ fluoroalkyl; in some embodiments $C_{1-10}$ fluoroalkyl; in some embodiments, trifluoromethyl.
In some embodiments of the above formulas, z>0 and at least one R$^x$ is F.
In some embodiments of the above formulas, z>0 and at least one R$^x$ is a $C_{1-20}$ alkyl; in some embodiments $C_{1-10}$ alkyl; in some embodiments, methyl.
In some embodiments of the above formulas, z>0 and at least one R$^x$ is a $C_{1-20}$ fluoroalkyl; in some embodiments $C_{1-10}$ fluoroalkyl; in some embodiments, trifluoromethyl.
In some embodiments of Formula I, m=0 and c=0-4.
In some embodiments of Formula I, m=1 and c=0-3.
In some embodiments of Formula I, n=0 and d=0-4.
In some embodiments of Formula I, n=1 and d=0-3.
In some embodiments of Formula I, c=0.
In some embodiments of Formula I, c=1.
In some embodiments of Formula I, c=2.
In some embodiments of Formula I, c=3.
In some embodiments of Formula I, c=4.
In some embodiments of Formula I, c>0.
In some embodiments of Formula I, c>0 and at least one R$^1$ is F.
In some embodiments of Formula I, c>0 and at least one R$^1$ is CN.
In some embodiments of Formula I, c>0 and at least one R$^1$ is a $C_{1-20}$ alkyl; in some embodiments $C_{1-10}$ alkyl.

In some embodiments of Formula I, c>0 and at least one R$^1$ is a $C_{1-20}$ fluoroalkyl; in some embodiments $C_{1-10}$ fluoroalkyl.
In some embodiments of Formula I, c>0 and at least one R$^1$ is a $C_{1-20}$ perfluorofluoroalkyl; in some embodiments $C_{1-10}$ perfluoroalkyl.
In some embodiments of Formula I, c>0 and at least one R$^1$ is a $C_{1-20}$ alkoxy; in some embodiments $C_{1-10}$ alkoxy.
In some embodiments of Formula I, c>0 and at least one R$^1$ is a $C_{1-20}$ fluoroalkoxy; in some embodiments $C_{1-10}$ fluoroalkoxy.
In some embodiments of Formula I, c>0 and at least one R$^1$ is a $C_{1-20}$ perfluoroalkoxy; in some embodiments $C_{1-10}$ perfluoroalkoxy.
In some embodiments of Formula I, c>0 and at least one R$^1$ is $SiH_3$.
In some embodiments of Formula I, c>0 and at least one R$^1$ is a $C_{1-12}$ silyl; in some embodiments $C_{3-6}$ silyl.
In some embodiments of Formula I, c>0 and at least one R$^1$ is a $C_{1-12}$ siloxy; in some embodiments $C_{3-6}$ siloxy.
In some embodiments of Formula I, c>0 and at least one R$^1$ is an unsubstituted or substituted $C_{6-30}$ hydrocarbon aryl; in some embodiments, an unsubstituted or substituted $C_{6-18}$ hydrocarbon aryl; in some embodiments, unsubstituted.
In some embodiments of Formula I, c>0 and at least one R$^1$ is an unsubstituted or substituted $C_{3-30}$ heteroaryl; in some embodiments, an unsubstituted or substituted $C_{3-18}$ heteroaryl; in some embodiments, unsubstituted.
In some embodiments of Formula I, c>0 and at least one R$^1$ is an unsubstituted or substituted $C_{6-30}$ hydrocarbon aryloxy; in some embodiments, an unsubstituted or substituted $C_{6-18}$ hydrocarbon aryloxy; in some embodiments, unsubstituted.
In some embodiments, any of the above hydrocarbon aryl, heteroaryl, and aryloxy groups are further substituted with one or more substituents selected from the group consisting of F, CN, alkyl, fluoroalkyl, alkoxy, fluoroalkoxy, silyl, and siloxy.
In some embodiments of Formula I, d=0.
In some embodiments of Formula I, d=1.
In some embodiments of Formula I, d=2.
In some embodiments of Formula I, d=3.
In some embodiments of Formula I, d=4.
In some embodiments of Formula I, d>0.
In some embodiments of Formula I, d>0 and at least one R$^2$ is F.
In some embodiments of Formula I, d>0 and at least one R$^2$ is CN.
In some embodiments of Formula I, d>0 and at least one R$^2$ is a $C_{1-20}$ alkyl; in some embodiments $C_{1-10}$ alkyl.
In some embodiments of Formula I, d>0 and at least one R$^2$ is a $C_{1-20}$ fluoroalkyl; in some embodiments $C_{1-10}$ fluoroalkyl.
In some embodiments of Formula I, d>0 and at least one R$^2$ is a $C_{1-20}$ perfluorofluoroalkyl; in some embodiments $C_{1-10}$ perfluoroalkyl.
In some embodiments of Formula I, d>0 and at least one R$^2$ is a $C_{1-20}$ alkoxy; in some embodiments $C_{1-10}$ alkoxy.
In some embodiments of Formula I, d>0 and at least one R$^2$ is a $C_{1-20}$ fluoroalkoxy; in some embodiments $C_{1-10}$ fluoroalkoxy.
In some embodiments of Formula I, d>0 and at least one R$^2$ is a $C_{1-20}$ perfluoroalkoxy; in some embodiments $C_{1-10}$ perfluoroalkoxy.
In some embodiments of Formula I, d>0 and at least one R$^2$ is $SiH_3$.

In some embodiments of Formula I, d>0 and at least one $R^2$ is a $C_{1-12}$ silyl; in some embodiments $C_{3-6}$ silyl.

In some embodiments of Formula I, d>0 and at least one $R^2$ is a $C_{1-12}$ siloxy; in some embodiments $C_{3-6}$ siloxy.

In some embodiments of Formula I, d>0 and at least one $R^2$ is an unsubstituted or substituted $C_{6-30}$ hydrocarbon aryl; in some embodiments, an unsubstituted or substituted $C_{6-18}$ hydrocarbon aryl; in some embodiments, unsubstituted.

In some embodiments of Formula I, d>0 and at least one $R^2$ is an unsubstituted or substituted $C_{3-30}$ heteroaryl; in some embodiments, an unsubstituted or substituted $C_{3-18}$ heteroaryl; in some embodiments, unsubstituted.

In some embodiments of Formula I, d>0 and at least one $R^2$ is an unsubstituted or substituted $C_{6-30}$ hydrocarbon aryloxy; in some embodiments, an unsubstituted or substituted $C_{6-18}$ hydrocarbon aryloxy; in some embodiments, unsubstituted.

In some embodiments, any of the above hydrocarbon aryl, heteroaryl, and aryloxy groups are further substituted with one or more substituents selected from the group consisting of F, CN, alkyl, fluoroalkyl, alkoxy, fluoroalkoxy, silyl, and siloxy.

In some embodiments of Formula I, $R^3 = R^4$.
In some embodiments of Formula I, $R^3 \neq R^4$.
In some embodiments of Formula I, $R^3 = R^4 = H$.
In some embodiments of Formula I, $R^3 = A^3$.
In some embodiments of Formula I, $R^3$ is H.
In some embodiments of Formula I, $R^3$ is F.
In some embodiments of Formula I, $R^3$ is CN.
In some embodiments of Formula I, $R^3$ is a $C_{1-20}$ alkyl; in some embodiments $C_{1-10}$ alkyl.

In some embodiments of Formula I, $R^3$ is a $C_{1-20}$ fluoroalkyl; in some embodiments $C_{1-10}$ fluoroalkyl.

In some embodiments of Formula I, $R^3$ is a $C_{1-20}$ perfluoroalkyl; in some embodiments $C_{1-10}$ perfluoroalkyl.

In some embodiments of Formula I, $R^3$ is a $C_{1-20}$ alkoxy; in some embodiments $C_{1-10}$ alkoxy.

In some embodiments of Formula I, $R^3$ is a $C_{1-20}$ fluoroalkoxy; in some embodiments $C_{1-10}$ fluoroalkoxy.

In some embodiments of Formula I, $R^3$ is a $C_{1-20}$ perfluoroalkoxy; in some embodiments $C_{1-10}$ perfluoroalkoxy.

In some embodiments of Formula I, $R^3$ is $SiH_3$.
In some embodiments of Formula I, $R^3$ is a $C_{1-12}$ silyl; in some embodiments $C_{3-6}$ silyl.

In some embodiments of Formula I, $R^3$ is a $C_{1-12}$ siloxy; in some embodiments $C_{3-6}$ siloxy.

In some embodiments of Formula I, $R^3$ is an unsubstituted or substituted $C_{6-30}$ hydrocarbon aryl; in some embodiments, a $C_{6-18}$ hydrocarbon aryl; in some embodiments, unsubstituted.

In some embodiments of Formula I, $R^3$ is an unsubstituted or substituted $C_{3-30}$ heteroaryl; in some embodiments, a $C_{3-18}$ heteroaryl; in some embodiments, unsubstituted.

In some embodiments of Formula I, $R^3$ is an unsubstituted or substituted $C_{6-30}$ hydrocarbon aryloxy; in some embodiments, a $C_{6-18}$ hydrocarbon aryloxy; in some embodiments, unsubstituted.

In some embodiments, any of the above hydrocarbon aryl, heteroaryl, and aryloxy groups are further substituted with one or more substituents selected from the group consisting of F, CN, alkyl, fluoroalkyl, alkoxy, fluoroalkoxy, silyl, and siloxy.

In some embodiments of Formula I, $R^4 = A^4$.
In some embodiments of Formula I, $R^4$ is H.
In some embodiments of Formula I, $R^4$ is F.
In some embodiments of Formula I, $R^4$ is CN.
In some embodiments of Formula I, $R^4$ is a $C_{1-20}$ alkyl; in some embodiments $C_{1-10}$ alkyl.

In some embodiments of Formula I, $R^4$ is a $C_{1-20}$ fluoroalkyl; in some embodiments $C_{1-10}$ fluoroalkyl.

In some embodiments of Formula I, $R^4$ is a $C_{1-20}$ perfluoroalkyl; in some embodiments $C_{1-10}$ perfluoroalkyl.

In some embodiments of Formula I, $R^4$ is a $C_{1-20}$ alkoxy; in some embodiments $C_{1-10}$ alkoxy.

In some embodiments of Formula I, $R^4$ is a $C_{1-20}$ fluoroalkoxy; in some embodiments $C_{1-10}$ fluoroalkoxy.

In some embodiments of Formula I, $R^4$ is a $C_{1-20}$ perfluoroalkoxy; in some embodiments $C_{1-10}$ perfluoroalkoxy.

In some embodiments of Formula I, $R^4$ is $SiH_3$.
In some embodiments of Formula I, $R^4$ is a $C_{1-12}$ silyl; in some embodiments $C_{3-6}$ silyl.

In some embodiments of Formula I, $R^4$ is a $C_{1-12}$ siloxy; in some embodiments $C_{3-6}$ siloxy.

In some embodiments of Formula I, $R^4$ is an unsubstituted or substituted $C_{6-30}$ hydrocarbon aryl; in some embodiments, a $C_{6-18}$ hydrocarbon aryl; in some embodiments, unsubstituted.

In some embodiments of Formula I, $R^4$ is an unsubstituted or substituted $C_{3-30}$ heteroaryl; in some embodiments, a $C_{3-18}$ heteroaryl; in some embodiments, unsubstituted.

In some embodiments of Formula I, $R^4$ is an unsubstituted or substituted $C_{6-30}$ hydrocarbon aryloxy; in some embodiments, a $C_{6-18}$ hydrocarbon aryloxy; in some embodiments, unsubstituted.

In some embodiments, any of the above hydrocarbon aryl, heteroaryl, and aryloxy groups are further substituted with one or more substituents selected from the group consisting of F, CN, alkyl, fluoroalkyl, alkoxy, fluoroalkoxy, silyl, and siloxy.

In some embodiments of Formula I, $R^5 = R^6$.
In some embodiments of Formula I, $R^5 \neq R^6$.
In some embodiments of Formula I, $R^5 = R^6 = H$.
In some embodiments of Formula I, $R^5$ is H.
In some embodiments of Formula I, $R^5$ is F.
In some embodiments of Formula I, $R^5$ is CN.
In some embodiments of Formula I, $R^5$ is a $C_{1-20}$ alkyl; in some embodiments $C_{1-10}$ alkyl.

In some embodiments of Formula I, $R^5$ is a $C_{1-20}$ fluoroalkyl; in some embodiments $C_{1-10}$ fluoroalkyl.

In some embodiments of Formula I, $R^5$ is a $C_{1-20}$ perfluoroalkyl; in some embodiments $C_{1-10}$ perfluoroalkyl.

In some embodiments of Formula I, $R^5$ is a $C_{1-20}$ alkoxy; in some embodiments $C_{1-10}$ alkoxy.

In some embodiments of Formula I, $R^5$ is a $C_{1-20}$ fluoroalkoxy; in some embodiments $C_{1-10}$ fluoroalkoxy.

In some embodiments of Formula I, $R^5$ is a $C_{1-20}$ perfluoroalkoxy; in some embodiments $C_{1-10}$ perfluoroalkoxy.

In some embodiments of Formula I, $R^5$ is $SiH_3$.
In some embodiments of Formula I, $R^5$ is a $C_{1-12}$ silyl; in some embodiments $C_{3-6}$ silyl.

In some embodiments of Formula I, $R^5$ is a $C_{1-12}$ siloxy; in some embodiments $C_{3-6}$ siloxy.

In some embodiments of Formula I, $R^5$ is an unsubstituted or substituted $C_{6-30}$ hydrocarbon aryl; in some embodiments, a $C_{6-18}$ hydrocarbon aryl; in some embodiments, unsubstituted.

In some embodiments of Formula I, $R^5$ is an unsubstituted or substituted $C_{3-30}$ heteroaryl; in some embodiments, a $C_{3-18}$ heteroaryl; in some embodiments, unsubstituted.

In some embodiments of Formula I, $R^5$ is an unsubstituted or substituted $C_{6-30}$ hydrocarbon aryloxy; in some embodiments, a $C_{6-18}$ hydrocarbon aryloxy; in some embodiments, unsubstituted.

In some embodiments, any of the above hydrocarbon aryl, heteroaryl, and aryloxy groups are further substituted with one or more substituents selected from the group consisting of F, CN, alkyl, fluoroalkyl, alkoxy, fluoroalkoxy, silyl, and siloxy.

All of the above-described embodiments for $R^5$ in Formula I, apply equally to $R^6$ in Formula I.

In some embodiments of Formula I, $R^8$ is a $C_{1-20}$ alkyl; in some embodiments $C_{1-10}$ alkyl.

In some embodiments of Formula I, $R^8$ is a $C_{1-12}$ silyl; in some embodiments $C_{3-6}$ silyl.

In some embodiments of Formula I, $R^8$ is an unsubstituted or substituted $C_{6-30}$ hydrocarbon aryl; in some embodiments, a $C_{6-18}$ hydrocarbon aryl; in some embodiments, unsubstituted.

In some embodiments of Formula I, $R^8$ is an unsubstituted or substituted $C_{3-30}$ heteroaryl; in some embodiments, a $C_{3-18}$ heteroaryl; in some embodiments, unsubstituted.

In some embodiments, any of the above hydrocarbon aryl and heteroaryl groups are further substituted with one or more substituents selected from the group consisting of F, CN, alkyl, fluoroalkyl, alkoxy, fluoroalkoxy, silyl, and siloxy.

In some embodiments of Formula I, $R^8$ has Formula b

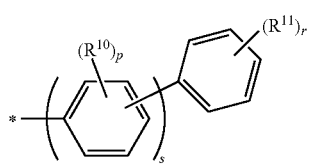

Formula b where:
$R^{10}$ and $R^{11}$ are the same or different at each occurrence and are selected from the group consisting of F, CN, alkyl, fluoroalkyl, unsubstituted or substituted hydrocarbon aryl, unsubstituted or substituted heteroaryl, alkoxy, fluoroalkoxy, unsubstituted or substituted aryloxy, silyl, and siloxy, where adjacent $R^{10}$ and/or $R^{11}$ groups may be joined together to form a fused ring;
p is an integer from 0-4;
r is an integer from 0-5;
s is an integer from 0-3; and
* indicates a point of attachment.

In some embodiments of Formula I, $R^8$ is selected from the group consisting of phenyl, biphenyl, and naphthyl, which can be unsubstituted or substituted.

In some embodiments of Formula I, $R^8$ is selected from the group consisting of phenyl, biphenyl, and naphthyl and has at least one substituent selected from the group consisting of F, alkyl, fluoroalkyl, alkoxy, and fluoroalkoxy.

In some embodiments of Formula I, the polyanhydride has Formula IA

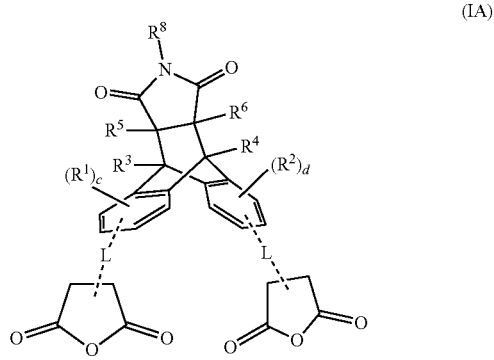

where $R^1$-$R^6$, $R^8$, L, c, d, and the single dashed lines are as defined in Formula I.

All of the above-described embodiments for $R^1$-$R^6$, $R^8$, L, c, and d in Formula I, apply equally to $R^1$-$R^6$, $R^8$, L, c, and d in Formula IA.

In some embodiments of Formula IA, $R^3 \neq A^3$.

In some embodiments of Formula IA, $R^4 \neq A^4$.

In some embodiments of Formula I, the polyanhydride has Formula IA-1

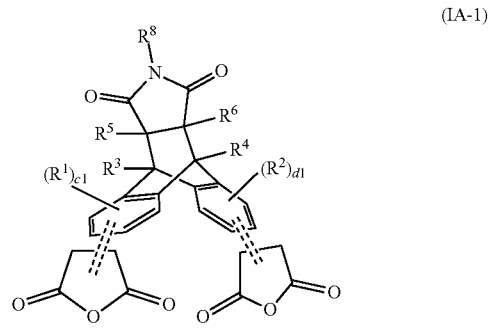

where:
c1 and d1 are the same or different and are an integer from 0-2; and
$R^1$-$R^6$, $R^8$, and the double dashed lines are as defined in Formula I.

All of the above-described embodiments for $R^1$-$R^6$, $R^8$ in Formula I, apply equally to $R^1$-$R^6$, $R^8$ in Formula IA-1.

In some embodiments of Formula IA-1, $R^3 \neq A^3$.
In some embodiments of Formula IA-1, $R^4 \neq A^4$.
In some embodiments of Formula IA-1, c1=0.
In some embodiments of Formula IA-1, c1=1.
In some embodiments of Formula IA-1, c1=2.
In some embodiments of Formula IA-1, c1>0.
In some embodiments of Formula IA-1, d1=0.
In some embodiments of Formula IA-1, d1=1.
In some embodiments of Formula IA-1, d1=2.
In some embodiments of Formula IA-1, d1>0.

In some embodiments of Formula I, the polyanhydride has Formula IA-1a

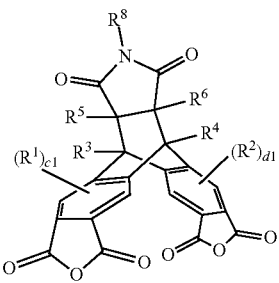

(IA-1a)

where $R^1$-$R^6$, $R^8$, c1, and d1 are as defined in Formula IA-1.

All of the above-described embodiments for $R^1$-$R^6$, $R^8$, c1, and d1 in Formula IA-1, apply equally to $R^1$-$R^6$, $R^8$, c1, and d1 in Formula IA-1a.

In some embodiments of Formula I, the polyanhydride has Formula IB

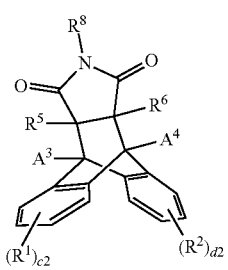

(IB)

where:
c2 and d2 are the same or different and are an integer from 0-4; and
$R^1$, $R^2$, $R^5$, $R^6$, $R^8$, $A^3$ and $A^4$ are as defined in Formula I.

All of the above-described embodiments for c and d in Formula I, apply equally to c2 and d2, respectively, in Formula IB.

All of the above-described embodiments for $R^1$, $R^2$, $R^5$, $R^6$, $R^8$, $A^3$ and $A^4$ in Formula I, apply equally to $R^1$, $R^2$, $R^5$, $R^6$, $R^8$, $A^3$ and $A^4$ in Formula IB.

In some embodiments of Formula I, the polyanhydride has Formula IB-1

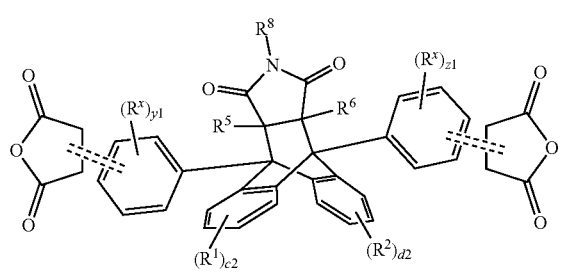

(IB-1)

where:
$R^x$ is the same or different at each occurrence and is selected from the group consisting of F, CN, alkyl, fluoroalkyl, alkoxy, fluoroalkoxy, silyl, and siloxy;
y1 and z1 are the same or different and are an integer from 0-3;
double dashed lines between two rings indicate that the rings are fused in any available position; and
$R^1$, $R^2$, $R^5$, $R^6$, $R^8$, c2 and d2 are as defined in Formula IB.

In some embodiments of Formula IB-1, y1=0.
In some embodiments of Formula IB-1, y1=1.
In some embodiments of Formula IB-1, y1=2.
In some embodiments of Formula IB-1, y1=3.
In some embodiments of Formula IB-1, y1>0.
In some embodiments of Formula IB-1, z1=0.
In some embodiments of Formula IB-1, z1=1.
In some embodiments of Formula IB-1, z1=2.
In some embodiments of Formula IB-1, z1=3.
In some embodiments of Formula IB-1, z1>0.

All of the above-described embodiments for $R^x$ in Formula I, apply equally to $R^x$ in Formula IB-1.

All of the above-described embodiments for $R^1$, $R^2$, $R^5$, $R^6$, $R^8$, c2 and d2 in Formula IB, apply equally to $R^1$, $R^2$, $R^5$, $R^6$, $R^8$, c2 and d2 in formula IB-1.

In some embodiments of Formula I, the polyanhydride has Formula IB-1a

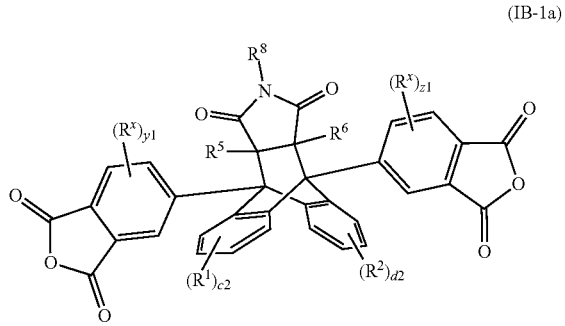

(IB-1a)

where $R^x$, $R^1$, $R^2$, $R^5$, $R^6$, $R^8$, c2, d2, y1, and z1 are as defined in Formula IB-1.

All of the above-described embodiments for $R^x$, $R^1$, $R^2$, $R^5$, $R^6$, $R^8$, c2, d2, y1, and z1 in Formula IB-1, apply equally to $R^x$, $R^1$, $R^2$, $R^5$, $R^6$, $R^8$, c2, d2, y1, and z1 in Formula IB-1a.

The new compounds can be made using any technique that will yield a C—C or C—N bond. A variety of such techniques are known, such as Suzuki, Yamamoto, Stille, Negishi, and metal-catalyzed C—N couplings as well as metal catalyzed and oxidative direct arylation, and Diels-Alder cycloaddition reactions. Exemplary preparations are given in the Examples.

One synthetic scheme is shown below.

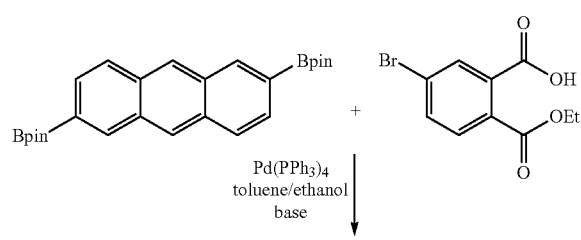

-continued

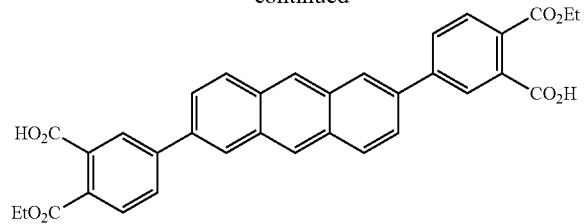

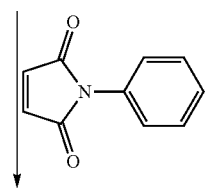

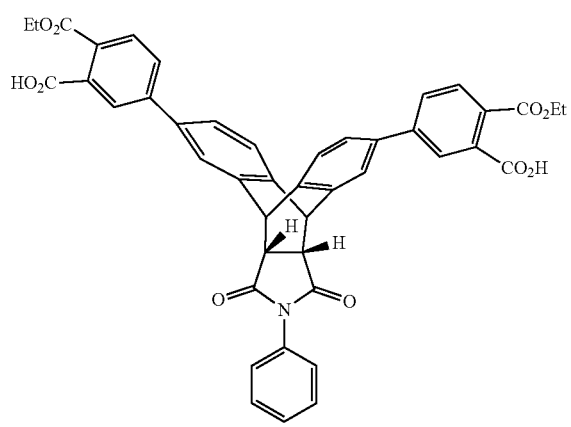

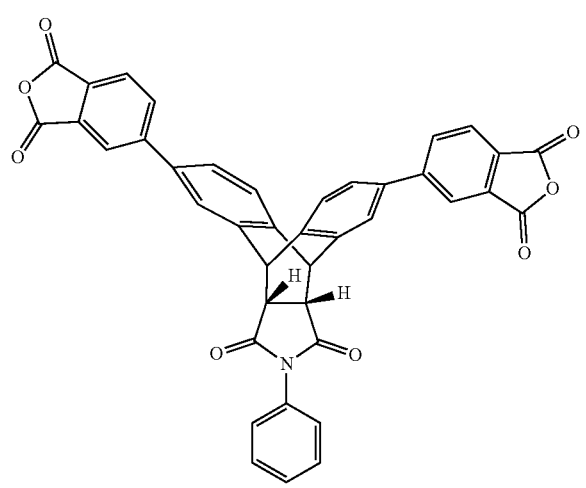

In the above scheme, "Bpin" represents boron pinacolate.

Any of the above embodiments for Formula I can be combined with one or more of the other embodiments, so long as they are not mutually exclusive. For example, the embodiment in which the polyanhydride has Formula IA can be combined with the embodiment in which $R^3=R^4$, and the embodiment in which $R^5=R^6=H$. The skilled person would understand which embodiments were mutually exclusive and would thus readily be able to determine the combinations of embodiments that are contemplated by the present application.

Some non-limiting examples of compounds having Formula I are shown below.

Compound 1

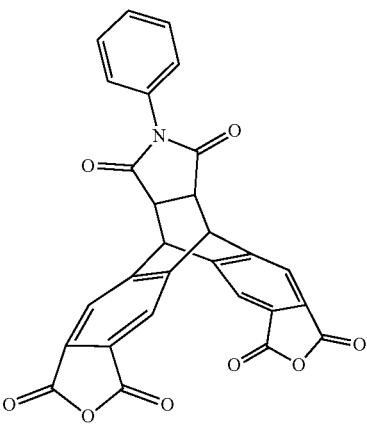

Compound 2

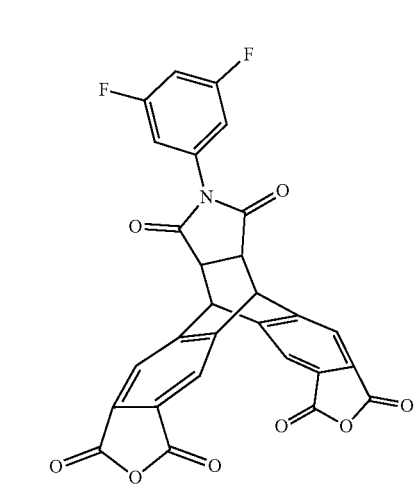

Compound 3

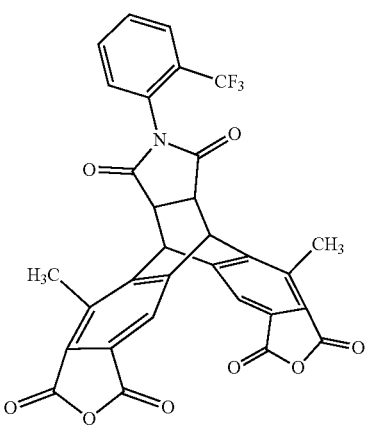

-continued

Compound 4

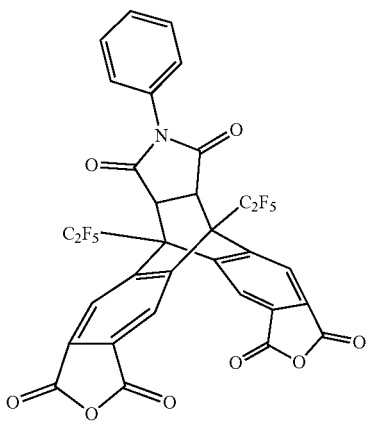

Compound 5

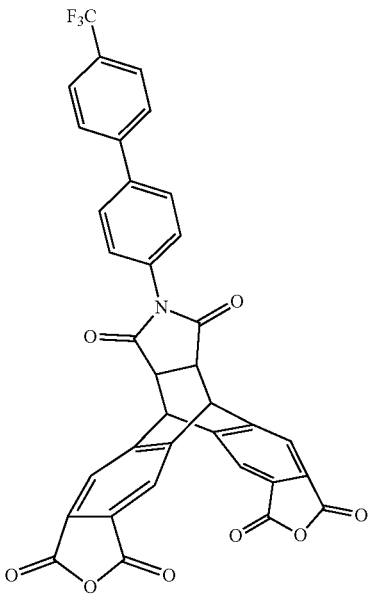

Compound 6

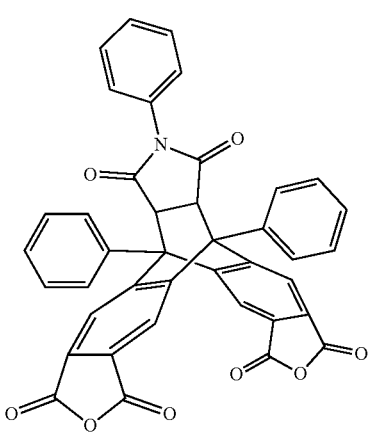

-continued

Compound 7

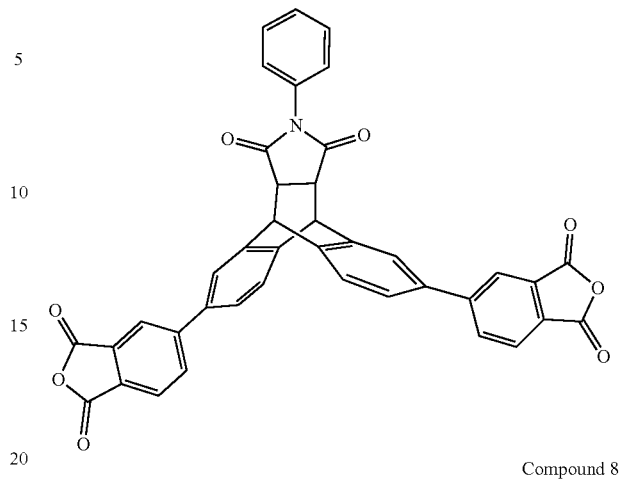

Compound 8

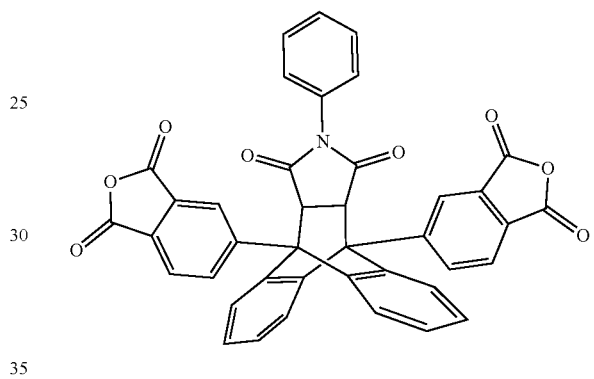

3. Polyamic Acid

The polyamic acid described herein is the reaction product of one or more polyanhydrides with one or more polyamines, wherein 10-100 mol % of the one or more polyanhydrides have Formula I.

In some embodiments of the polyamic acid, a single polyanhydride having Formula I is reacted.

In some embodiments of the polyamic acid, two different polyanhydrides having Formula I are reacted.

In some embodiments of the polyamic acid, three different polyanhydrides having Formula I are reacted.

In some embodiments of the polyamic acid, four different polyanhydrides having Formula I are reacted.

In some embodiments of the polyamic acid, 20-100 mol % of the one or more polyanhydrides have Formula I; in some embodiments, 30-100 mol %; in some embodiments, 40-100 mol %; in some embodiments, 50-100 mol %; in some embodiments, 60-100 mol %; in some embodiments, 70-100 mol %; in some embodiments, 80-100 mol %; in some embodiments, 90-100 mol %; in some embodiments, 100%.

In some embodiments of the polyamic acid, at least one additional polyanhydride is reacted with the polyanhydride(s) having Formula I.

In some embodiments of the polyamic acid, one additional polyanhydride is reacted with the polyanhydride(s) having Formula I.

In some embodiments of the polyamic acid, two additional polyanhydrides are reacted with the polyanhydride(s) having Formula I.

In some embodiments of the polyamic acid, three additional polyanhydrides are reacted with the polyanhydride(s) having Formula I.

In some embodiments of the polyamic acid, four additional polyanhydrides are reacted with the polyanhydride(s) having Formula I.

In some embodiments of the polyamic acid, the polyamic acid has a repeat unit structure of Formula II

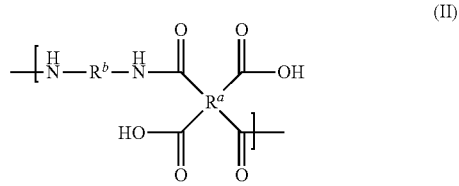

(II)

where:

$R^a$ is the same or different at each occurrence and represents one or more tetracarboxylic acid component residues; and $R^b$ is the same or different at each occurrence and represents one or more aromatic diamine residues;

wherein 10-100 mol % of $R^a$ is a residue from one or more dianhydrides having Formula I.

In Formula II, 10-100 mol % of $R^a$ represents a dianhydride residue from one or more dianhydrides having Formula I, as shown above.

In some embodiments of Formula II, 10-100 mol % of $R^a$ represents a dianhydride residue from one dianhydride having Formula I, as shown above.

In some embodiments of Formula II, 10-100 mol % of $R^a$ represents a dianhydride residue from two different dianhydrides which both have Formula I, as shown above.

In some embodiments of Formula II, 10-100 mol % of $R^a$ represents a dianhydride residue from three different dianhydrides which all have Formula I, as shown above.

In some embodiments of Formula II, 10-100 mol % of $R^a$ represents a dianhydride residue from four or more different dianhydrides which all have Formula I, as shown above.

In some embodiments of Formula II, 20-100 mol % of $R^a$ is a residue from one or more dianhydrides having Formula I; in some embodiments, 30-100 mol %; in some embodiments, 40-100 mol %; in some embodiments, 50-100 mol %; in some embodiments, 60-100 mol %; in some embodiments, 70-100 mol %; in some embodiments, 80-100 mol %; in some embodiments, 90-100 mol %; in some embodiments, 100%.

Any of the above embodiments for Formula I in Formula II can be combined with one or more of the other embodiments, so long as they are not mutually exclusive.

In some embodiments of Formula II, $R^a$ represents a dianhydride residue from one or more dianhydrides having Formula I and at least one additional dianhydride residue.

In some embodiments of Formula II, $R^a$ represents a dianhydride residue from one or more dianhydrides having Formula I and one additional dianhydride residue.

In some embodiments of Formula II, $R^a$ represent a dianhydride residue from one or more dianhydrides having Formula I and two additional dianhydride residues.

In some embodiments of Formula II, $R^a$ represents a dianhydride residue from one or more dianhydrides having Formula I and three additional dianhydride residues.

In some embodiments, the additional dianhydride residue is the residue from a dianhydride selected from the group consisting of pyromellitic dianhydride (PMDA), 3,3',4,4'-biphenyl tetracarboxylic dianhydride (BPDA), 4,4'-oxydiphthalic anhydride (ODPA), 4,4'-hexafluoroiso-propylidenebisphthalic dianhydride (6FDA), 3,3',4,4'-benzophenone tetracarboxylic dianhydride (BTDA), 3,3',4,4'-diphenylsulfone tetracarboxylic dianhydride (DSDA), 4,4'-bisphenol-A dianhydride (BPADA), hydroquinone diphthalic anhydride (HQDEA), ethylene glycol bis (trimellitic anhydride) (TMEG-100), dioxotetrahydrofuran-3-yl)-1,2,3,4-tetrahydronapthalene-1,2-dicarboyxlic anhydride (DTDA); 4,4'-bisphenol A dianhydride (BPADA), and the like and combinations thereof. These aromatic dianhydrides may optionally be substituted with groups that are known in the art including alkyl, aryl, nitro, cyano, —N(R')(R''), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxy, siloxane, thioalkoxy, —S(O)$_2$—, —C(=O)—N(R')(R''), (R')(R'')N-alkyl, (R')(R'')N-alkoxyalkyl, (R')(R'')N-alkylaryloxyalkyl, —S(O)$_s$-aryl (where s=0-2) or —S(O)$_s$-heteroaryl (where s=0-2). Each R' and R'' is independently an optionally substituted alkyl, cycloalkyl, or aryl group. R' and R'', together with the nitrogen atom to which they are bound, can form a ring system in certain embodiments. Substituents may also be crosslinking groups.

In some embodiments of Formula II, the additional dianhydride residue is from one or more tetracarboxylic acid dianhydrides selected from the group consisting of PMDA, BPDA, 6FDA, and BTDA.

In some embodiments of Formula II, $R^b$ represents a single diamine residue.

In some embodiments of Formula II, $R^b$ represents two diamine residues.

In some embodiments of Formula II, $R^b$ represents three diamine residues.

In some embodiments of Formula II, $R^b$ represents four diamine residues.

In some embodiments of Formula II, $R^b$ represents one or more diamine residues.

Examples of suitable aromatic diamines include, but are not limited to, p-phenylene diamine (PPD), 2,2'-dimethyl-4,4'-diaminobiphenyl (m-tolidine), 3,3'-dimethyl-4,4'-diaminobiphenyl (o-tolidine), 3,3'-dihydroxy-4,4'-diaminobiphenyl (HAB), 9,9'-bis(4-aminophenyl)fluorene (FDA), o-tolidine sulfone (TSN), 2,3,5,6-tetramethyl-1,4-phenylenediamine (TMPD), 2,4-diamino-1,3,5-trimethyl benzene (DAM), 3,3',5,5'-tetramethylbenzidine (3355TMB), 2,2'-bis(trifluoromethyl) benzidine (22TFMB or TFMB), 2,2-bis[4-(4-aminophenoxy)phenyl]propane (BAPP), 4,4'-methylene dianiline (MDA), 4,4'[1,3-phenylenebis(1-methyl-ethylidene)]bisaniline (Bis-M), 4,4'-[1,4-phenylenebis(1-methyl-ethylidene)]bisaniline (Bis-P), 4,4'-oxydianiline (4,4'-ODA), m-phenylene diamine (MPD), 3,4'-oxydianiline (3,4'-ODA), 3,3'-diaminodiphenyl sulfone (3,3'-DDS), 4,4'-diaminodiphenyl sulfone (4,4'-DDS), 4,4'-diaminodiphenyl sulfide (ASD), 2,2-bis[4-(4-amino-phenoxy)phenyl]sulfone (BAPS), 2,2-bis[4-(3-aminophenoxy)phenyl]sulfone (m-BAPS), 1,4'-bis(4-aminophenoxy)benzene (TPE-Q), 1,3'-bis(4-aminophenoxy)benzene (TPE-R), 1,3'-bis(4-amino-phenoxy)benzene (APB-133), 4,4'-bis(4-aminophenoxy)biphenyl (BARB), 4,4'-diaminobenzanilide (DABA), methylene bis(anthranilic acid) (MBAA), 1,3'-bis(4-aminophenoxy)-2,2-dimethylpropane (DANPG), 1,5-bis(4-aminophenoxy)pentane (DASMG), 2,2'-bis[4-(4-aminophenoxy pehnyl)]hexafluoropropane (HFBAPP), 2,2-bis(4-aminophenyl) hexafluoropropane (Bis-A-AF), 2,2-bis(3-amino-4-hydroxyphenyl) hexafluoropropane (Bis-AP-AF), 2,2-bis(3-amino-4-methylphenyl) hexafluoropropane (Bis-AT-AF), 4,4'-bis(4-amino-2-trifluoromethyl phenoxy)biphenyl (6BFBAPB), 3,3'5,5'-tetramethyl-4,4'-diamino diphenylmethane (TMMDA), and the like and combinations thereof.

In some embodiments of Formula II, $R^b$ represents a diamine residue from one or more diamines selected from the group consisting of PPD, 4,4'-ODA, 3,4'-ODA, TFMB, Bis-A-AF, Bis-AT-AF, and Bis-P.

In some embodiments of Formula II, moieties resulting from monoanhydride monomers are present as end-capping groups.

In some embodiments, the monoanhydride monomers are selected from the group consisting of phthalic anhydrides and the like and derivatives thereof.

In some embodiments, the monoanhydrides are present at an amount up to 5 mol % of the total tetracarboxylic acid composition.

In some embodiments of Formula II, moieties resulting from monoamine monomers are present as end-capping groups.

In some embodiments, the monoamine monomers are selected from the group consisting of aniline and the like and derivatives thereof.

In some embodiments, the monoamines are present at an amount up to 5 mol % of the total amine composition.

In some embodiments, the polyamic acid has a weight average molecular weight (Mw) greater than 100,000 based on gel permeation chromatography with polystyrene standards.

In some embodiments, the polyamic acid has a weight average molecular weight (Mw) greater than 150,000 based on gel permeation chromatography with polystyrene standards.

In some embodiments, the polyamic acid has a molecular weight (Mw) greater than 200,000 based on gel permeation chromatography with polystyrene standards.

In some embodiments, the polyamic acid has a weight average molecular weight (Mw) greater than 250,000 based on gel permeation chromatography with polystyrene standards.

In some embodiments, the polyamic acid has a weight average molecular weight (Mw) greater than 300,000 based on gel permeation chromatography with polystyrene standards.

In some embodiments, the polyamic acid has a weight average molecular weight (Mw) between 100,000 and 400,000 based on gel permeation chromatography with polystyrene standards.

In some embodiments, the polyamic acid has a weight average molecular weight (Mw) between 200,000 and 400,000 based on gel permeation chromatography with polystyrene standards.

In some embodiments, the polyamic acid has a weight average molecular weight (Mw) between 250,000 and 350,000 based on gel permeation chromatography with polystyrene standards.

In some embodiments, the polyamic acid has a weight average molecular weight (Mw) between 200,000 and 300,000 based on gel permeation chromatography with polystyrene standards.

Any of the above embodiments for the polyamic acid can be combined with one or more of the other embodiments, so long as they are not mutually exclusive.

Overall polyamic acid compositions can be designated via the notation commonly used in the art. For example, a polyamic acid having a tetracarboxylic acid component that is 100% ODPA, and a diamine component that is 90 mol % Bis-P and 10 mol % TFMB, would be represented as:

ODPA//Bis-P/22TFMB 100//90/10.

There is also provided a liquid composition comprising (a) the polyamic acid having a repeat unit of Formula II, and (b) a high-boiling aprotic solvent. The liquid composition is also referred to herein as the "polyamic acid solution".

In some embodiments, the high-boiling aprotic solvent has a boiling point of 150° C. or higher.

In some embodiments, the high-boiling aprotic solvent has a boiling point of 175° C. or higher.

In some embodiments, the high-boiling aprotic solvent has a boiling point of 200° C. or higher.

In some embodiments, the high-boiling aprotic solvent is a polar solvent. In some embodiments, the solvent has a dielectric constant greater than 20.

Some examples of high-boiling aprotic solvents include, but are not limited to, N-methyl-2-pyrrolidone (NMP), dimethyl acetamide (DMAc), dimethyl sulfoxide (DMSO), dimethyl formamide (DMF), γ-butyrolactone, dibutyl carbitol, butyl carbitol acetate, diethylene glycol monoethyl ether acetate, propylene glycol monomethyl ether acetate and the like, and combinations thereof.

In some embodiments of the liquid composition, the solvent is selected from the group consisting of NMP, DMAc, and DMF.

In some embodiments of the liquid composition, the solvent is NMP.

In some embodiments of the liquid composition, the solvent is DMAc.

In some embodiments of the liquid composition, the solvent is DMF.

In some embodiments of the liquid composition, the solvent is γ-butyrolactone.

In some embodiments of the liquid composition, the solvent is dibutyl carbitol.

In some embodiments of the liquid composition, the solvent is butyl carbitol acetate.

In some embodiments of the liquid composition, the solvent is diethylene glycol monoethyl ether acetate.

In some embodiments of the liquid composition, the solvent is propylene glycol monoethyl ether acetate.

In some embodiments, more than one of the high-boiling aprotic solvents identified above is used in the liquid composition.

In some embodiments, additional cosolvents are used in the liquid composition.

In some embodiments, the liquid composition is <1 weight % polyamic acid in >99 weight % high-boiling aprotic solvent.

In some embodiments, the liquid composition is 1-5 weight % polyamic acid in 95-99 weight % high-boiling aprotic solvent.

In some embodiments, the liquid composition is 5-10 weight % polyamic acid in 90-95 weight % high-boiling aprotic solvent.

In some embodiments, the liquid composition is 10-15 weight % polyamic acid in 85-90 weight % high-boiling aprotic solvent.

In some embodiments, the liquid composition is 15-20 weight % polyamic acid in 80-85 weight % high-boiling aprotic solvent.

In some embodiments, the liquid composition is 20-25 weight % polyamic acid in 75-80 weight % high-boiling aprotic solvent.

In some embodiments, the liquid composition is 25-30 weight % polyamic acid in 70-75 weight % high-boiling aprotic solvent.

In some embodiments, the liquid composition is 30-35 weight % polyamic acid in 65-70 weight % high-boiling aprotic solvent.

In some embodiments, the liquid composition is 35-40 weight % polyamic acid in 60-65 weight % high-boiling aprotic solvent.

In some embodiments, the liquid composition is 40-45 weight % polyamic acid in 55-60 weight % high-boiling aprotic solvent.

In some embodiments, the liquid composition is 45-50 weight % polyamic acid in 50-55 weight % high-boiling aprotic solvent.

In some embodiments, the liquid composition is 50 weight % polyamic acid in 50 weight % high-boiling aprotic solvent.

The polyamic acid solutions can optionally further contain any one of a number of additives. Such additives can be: antioxidants, heat stabilizers, adhesion promoters, coupling agents (e.g. silanes), inorganic fillers or various reinforcing agents so long as they don't adversely impact the desired polyimide properties.

The polyamic acid solutions can be prepared using a variety of available methods with respect to the introduction of the components (i.e., the monomers and solvents). Some methods of producing a polyamic acid solution include:

(a) a method wherein the polyamine components and polyanhydride components are preliminarily mixed together and then the mixture is added in portions to a solvent while stirring.

(b) a method wherein a solvent is added to a stirring mixture of polyamine and polyanhydride components. (contrary to (a) above)

(c) a method wherein polyamines are exclusively dissolved in a solvent and then polyanhydrides are added thereto at such a ratio as allowing to control the reaction rate.

(d) a method wherein the polyanhydride components are exclusively dissolved in a solvent and then amine components are added thereto at such a ratio to allow control of the reaction rate.

(e) a method wherein the components and the polyanhydride components are separately dissolved in solvents and then these solutions are mixed in a reactor.

(f) a method wherein the polyamic acid with excessive polyamine component and another polyamic acid with excessive polyanhydride component are preliminarily formed and then reacted with each other in a reactor, particularly in such a way as to create a non-random or block copolymer.

(g) a method wherein a specific portion of the polyamine components and the polyanhydride components are first reacted and then the residual polyamine components are reacted, or vice versa.

(h) a method wherein the components are added in part or in whole in any order to either part or whole of the solvent, also where part or all of any component can be added as a solution in part or all of the solvent.

(i) a method of first reacting one of the polyanhydride components with one of the polyamine components giving a first polyamic acid. Then reacting the other polyanhydride component with the other polyamine component to give a second polyamic acid. Then combining the polyamic acids in any one of a number of ways prior to film formation.

Generally speaking, a polyamic acid solution can be obtained from any one of the polyamic acid solution preparation methods disclosed above.

The polyamic acid solution can then be filtered one or more times in order to reduce the particle content. The polyimide film generated from such a filtered solution can show a reduced number of defects and thereby lead to superior performance in the electronics applications disclosed herein. An assessment of the filtration efficiency can be made by the laser particle counter test wherein a representative sample of the polyamic acid solution is cast onto a 5" silicon wafer. After soft baking/drying, the film is evaluated for particle content by any number of laser particle counting techniques on instruments that are commercially available and known in the art.

In some embodiments, the polyamic acid solution is prepared and filtered to yield a particle content of less than 40 particles as measured by the laser particle counter test.

In some embodiments, the polyamic acid solution is prepared and filtered to yield a particle content of less than 30 particles as measured by the laser particle counter test.

In some embodiments, the polyamic acid solution is prepared and filtered to yield a particle content of less than 20 particles as measured by the laser particle counter test.

In some embodiments, the polyamic acid solution is prepared and filtered to yield a particle content of less than 10 particles as measured by the laser particle counter test.

In some embodiments, the polyamic acid solution is prepared and filtered to yield particle content of between 2 particles and 8 particles as measured by the laser particle counter test.

In some embodiments, the polyamic acid solution is prepared and filtered to yield particle content of between 4 particles and 6 particles as measured by the laser particle counter test.

Exemplary preparations of polyamic acid solutions are given in the examples.

4. Polyimide Having the Repeat Unit Structure of Formula III

There is provided a polyimide resulting from imidization of the above-described polyamic acid. By "imidization" is meant intramolecular cyclization of the amic acid groups to form imide groups. In some embodiments, thermal imidization is used. In some embodiments, chemical imidization is used. In some embodiments, a combination of thermal and chemical imidization is used.

In some embodiments, the polyimide has a repeat unit structure of Formula III

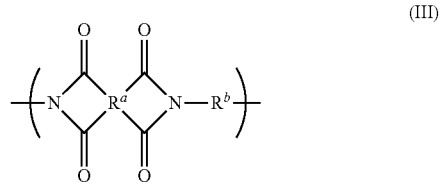

(III)

where $R^a$ is the same or different at each occurrence and represents one or more tetracarboxylic acid component residues; and $R^b$ is the same or different at each occurrence and represents one or more aromatic diamine residues;

wherein 10-100 mol % of $R^a$ is a residue from one or more dianhydrides having Formula I.

All of the above-described embodiments for $R^a$ and $R^b$ in Formula II apply equally to $R^a$ and $R^b$ in Formula III.

Any of the above embodiments for Formula I in Formula III can be combined with one or more of the other embodiments, so long as they are not mutually exclusive.

Polyimides can be made from any suitable polyimide precursor such as a polyamic acid, a polyamic acid ester, a polyisoimide, and a polyamic acid salt.

There is also provided a polyimide film, wherein the polyimide has a repeat unit structure of Formula III, as described above.

Polyimide films can be made by coating a polyimide precursor onto a substrate and subsequently imidizing. This can be accomplished by a thermal conversion process or a chemical conversion process.

Further, if the polyimide is soluble in suitable coating solvents, it can be provided as an already-imidized polymer dissolved in the suitable coating solvent and coated as the polyimide.

In some embodiments, the polyimide film comprising a polyimide having repeat units of Formula III has both a high glass transition temperature and a low optical retardation, as well as low color.

In some embodiments of the polyimide film, the glass transition temperature (T g) is greater than 300° C. for a polyimide film cured at a temperature above 350° C., in some embodiments, greater than 370° C., in some embodiments, greater than 380° C.

In some embodiments of the polyimide film, the optical retardation is less than 120 at 550 nm; in some embodiments, less than 100; in some embodiments, less than 90.

In some embodiments of the polyimide film, the in-plane coefficient of thermal expansion (CTE) is less than 45 ppm/° C. between 50° C. and 200° C., for the first measurement; in some embodiments, less than 30 ppm/° C., in some embodiments, less than 20 ppm/° C., in some embodiments, less than 15 ppm/° C.

In some embodiments of the polyimide film, the in-plane coefficient of thermal expansion (CTE) is less than 75 ppm/° C. between 50° C. and 200° C., for the second measurement; in some embodiments, less than 65 ppm/° C.

In some embodiments of the polyimide film, the 1% TGA weight loss temperature is greater than 350° C., in some embodiments, greater than 400° C., in some embodiments, greater than 450° C.

In some embodiments of the polyimide film, the tensile modulus is between 1.5 GPa and 15.0 GPa; in some embodiments, between 1.5 GPa and 10.0 GPa; in some embodiments, between 1.5 and 7.5 GPa; in some embodiments, between 1.5 and 5.0 GPa.

In some embodiments of the polyimide film, the elongation to break is greater than 10%.

In some embodiments of the polyimide film, the haze is less than 1.0%; in some embodiments less than 0.5%.

In some embodiments of the polyimide film, the b* is less than 7.5; in some embodiments, less than 5.0.

In some embodiments of the polyimide film, the YI is less than 12; in some embodiments, less than 10.

In some embodiments of the polyimide film, the transmittance at 400 nm is greater than 40%; in some embodiments, greater than 50%.

In some embodiments of the polyimide film, the transmittance at 430 nm is greater than 60%; in some embodiments, greater than 70%.

In some embodiments of the polyimide film, the transmittance at 450 nm is greater than 70%; in some embodiments, greater than 80%.

In some embodiments of the polyimide film, the transmittance at 550 nm is greater than 70%; in some embodiments, greater than 80%.

In some embodiments of the polyimide film, the transmittance at 750 nm is greater than 70%; in some embodiments, greater than 80%.

Any of the above embodiments for the polyimide film can be combined with one or more of the other embodiments, so long as they are not mutually exclusive.

5. Methods for Preparing the Polyimide Films

Generally, polyimide films can be prepared from polyimide precursors by chemical or thermal conversion. In some embodiments, the films are prepared from the corresponding polyamic acid solutions by chemical or thermal conversion processes. The polyimide films disclosed herein, particularly when used as flexible replacements for glass in electronic devices, are prepared by thermal conversion processes.

Generally, polyimide films can be prepared from the corresponding polyamic acid solutions by chemical or thermal conversion processes. The polyimide films disclosed herein, particularly when used as flexible replacements for glass in electronic devices, are prepared by thermal conversion or modified-thermal conversion processes, versus chemical conversion processes.

Chemical conversion processes are described in U.S. Pat. Nos. 5,166,308 and 5,298,331 which are incorporated by reference in their entirety. In such processes, conversion chemicals are added to the polyamic acid solutions. The conversion chemicals found to be useful in the present invention include, but are not limited to, (i) one or more dehydrating agents, such as, aliphatic acid anhydrides (acetic anhydride, etc.) and acid anhydrides; and (ii) one or more catalysts, such as, aliphatic tertiary amines (triethylamine, etc.), tertiary amines (dimethylaniline, etc.) and heterocyclic tertiary amines (pyridine, picoline, isoquinoilne, etc.). The anhydride dehydrating material is typically used in a slight molar excess of the amount of amide acid groups present in the polyamic acid solution. The amount of acetic anhydride used is typically about 2.0-3.0 moles per equivalent of the polyamic acid. Generally, a comparable amount of tertiary amine catalyst is used.

Thermal conversion processes may or may not employ conversion chemicals (i.e., catalysts) to convert a polyamic acid casting solution to a polyimide. If conversion chemicals are used, the process may be considered a modified-thermal conversion process. In both types of thermal conversion processes, only heat energy is used to heat the film to both dry the film of solvent and to perform the imidization reaction. Thermal conversion processes with or without conversion catalysts are generally used to prepare the polyimide films disclosed herein.

Specific method parameters are pre-selected considering that it is not just the film composition that yields the properties of interest. Rather, the cure temperature and temperature-ramp profile also play important roles in the achievement of the most desirable properties for the intended uses disclosed herein. The polyamic acids should be imidized at a temperature at, or higher than, the highest temperature of any subsequent processing steps (e.g. deposition of inorganic or other layer(s) necessary to produce a functioning display), but at a temperature which is lower than the temperature at which significant thermal degradation/discoloration of the polyimide occurs. It should also be noted that an inert atmosphere is generally preferred, particularly when higher processing temperatures are employed for imidization.

For the polyamic acids/polyimides disclosed herein, temperatures of 300° C. to 320° C. are typically employed when subsequent processing temperatures in excess of 300° C. are required. Choosing the proper curing temperature allows a fully cured polyimide which achieves the best balance of thermal and mechanical properties. Because of this very high temperature, an inert atmosphere is required. Typically, oxygen levels in the oven of <100 ppm should be employed. Very low oxygen levels enable the highest curing temperatures to be used without significant degradation/discoloration of the polymer. Catalysts that accelerate the imidization process are effective at achieving higher levels of imidization at cure temperatures between about 200° C. and 300° C. This approach may be optionally employed if the flexible device is prepared with upper cure temperatures that are below the T g of the polyimide.

The amount of time in each potential cure step is also an important process consideration. Generally, the time used for the highest-temperature curing should be kept to a minimum. For 320° C. cure, for example, cure time can be up to an hour or so under an inert atmosphere; but at higher cure temperatures, this time should be shortened to avoid thermal degradation. Generally speaking, higher temperature dictates shorter time. Those skilled in the art will recognize the balance between temperature and time in order to optimize the properties of the polyimide for a particular end use.

In some embodiments, the polyamic acid solution is converted into a polyimide film via a thermal conversion process.

In some embodiments of the thermal conversion process, the polyamic acid solution is coated onto the matrix such that the soft-baked thickness of the resulting film is less than 50 μm.

In some embodiments of the thermal conversion process, the polyamic acid solution is coated onto the matrix such that the soft-baked thickness of the resulting film is less than 40 μm.

In some embodiments of the thermal conversion process, the polyamic acid solution is coated onto the matrix such that the soft-baked thickness of the resulting film is less than 30 μm.

In some embodiments of the thermal conversion process, the polyamic acid solution is coated onto the matrix such that the soft-baked thickness of the resulting film is less than 20 μm.

In some embodiments of the thermal conversion process, the polyamic acid solution is coated onto the matrix such that the soft-baked thickness of the resulting film is between 10 μm and 20 μm.

In some embodiments of the thermal conversion process, the polyamic acid solution is coated onto the matrix such that the soft-baked thickness of the resulting film is between 15 μm and 20 μm.

In some embodiments of the thermal conversion process, the polyamic acid solution is coated onto the matrix such that the soft-baked thickness of the resulting film is 18 μm.

In some embodiments of the thermal conversion process, the polyamic acid solution is coated onto the matrix such that the soft-baked thickness of the resulting film is less than 10 μm.

In some embodiments of the thermal conversion process, the coated matrix is soft baked on a hot plate in proximity mode wherein nitrogen gas is used to hold the coated matrix just above the hot plate.

In some embodiments of the thermal conversion process, the coated matrix is soft baked on a hot plate in full-contact mode wherein the coated matrix is in direct contact with the hot plate surface.

In some embodiments of the thermal conversion process, the coated matrix is soft baked on a hot plate using a combination of proximity and full-contact modes.

In some embodiments of the thermal conversion process, the coated matrix is soft-baked using a hot plate set at 80° C.

In some embodiments of the thermal conversion process, the coated matrix is soft-baked using a hot plate set at 90° C.

In some embodiments of the thermal conversion process, the coated matrix is soft-baked using a hot plate set at 100° C.

In some embodiments of the thermal conversion process, the coated matrix is soft-baked using a hot plate set at 110° C.

In some embodiments of the thermal conversion process, the coated matrix is soft-baked using a hot plate set at 120° C.

In some embodiments of the thermal conversion process, the coated matrix is soft-baked using a hot plate set at 130° C.

In some embodiments of the thermal conversion process, the coated matrix is soft-baked using a hot plate set at 140° C.

In some embodiments of the thermal conversion process, the coated matrix is soft-baked for a total time of more than 10 minutes.

In some embodiments of the thermal conversion process, the coated matrix is soft-baked for a total time of less than 10 minutes.

In some embodiments of the thermal conversion process, the coated matrix is soft-baked for a total time of less than 8 minutes.

In some embodiments of the thermal conversion process, the coated matrix is soft-baked for a total time of less than 6 minutes.

In some embodiments of the thermal conversion process, the coated matrix is soft-baked for a total time of 4 minutes.

In some embodiments of the thermal conversion process, the coated matrix is soft-baked for a total time of less than 4 minutes.

In some embodiments of the thermal conversion process, the coated matrix is soft-baked for a total time of less than 2 minutes.

In some embodiments of the thermal conversion process, the soft-baked coated matrix is subsequently cured at 2 pre-selected temperatures for 2 pre-selected time intervals, the latter of which may be the same or different.

In some embodiments of the thermal conversion process, the soft-baked coated matrix is subsequently cured at 3 pre-selected temperatures for 3 pre-selected time intervals, each of which of the latter of which may be the same or different.

In some embodiments of the thermal conversion process, the soft-baked coated matrix is subsequently cured at 4 pre-selected temperatures for 4 pre-selected time intervals, each of which of the latter of which may be the same or different.

In some embodiments of the thermal conversion process, the soft-baked coated matrix is subsequently cured at 5 pre-selected temperatures for 5 pre-selected time intervals, each of which of the latter of which may be the same or different.

In some embodiments of the thermal conversion process, the soft-baked coated matrix is subsequently cured at 6 pre-selected temperatures for 6 pre-selected time intervals, each of which of the latter of which may be the same or different.

In some embodiments of the thermal conversion process, the soft-baked coated matrix is subsequently cured at 7 pre-selected temperatures for 7 pre-selected time intervals, each of which of the latter of which may be the same or different.

In some embodiments of the thermal conversion process the soft-baked coated matrix is subsequently cured at 8 pre-selected temperatures for 8 pre-selected time intervals, each of which of the latter of which may be the same or different.

In some embodiments of the thermal conversion process, the soft-baked coated matrix is subsequently cured at 9 pre-selected temperatures for 9 pre-selected time intervals, each of which of the latter of which may be the same or different.

In some embodiments of the thermal conversion process, the soft-baked coated matrix is subsequently cured at 10 pre-selected temperatures for 10 pre-selected time intervals, each of which of the latter of which may be the same or different.

In some embodiments of the thermal conversion process, the pre-selected temperature is greater than 80° C.

In some embodiments of the thermal conversion process, the pre-selected temperature is equal to 100° C.

In some embodiments of the thermal conversion process, the pre-selected temperature is greater than 100° C.

In some embodiments of the thermal conversion process, the pre-selected temperature is equal to 150° C.

In some embodiments of the thermal conversion process, the pre-selected temperature is greater than 150° C.

In some embodiments of the thermal conversion process, the pre-selected temperature is equal to 200° C.

In some embodiments of the thermal conversion process, the pre-selected temperature is greater than 200° C.

In some embodiments of the thermal conversion process, the pre-selected temperature is equal to 250° C.

In some embodiments of the thermal conversion process, the pre-selected temperature is greater than 250° C.

In some embodiments of the thermal conversion process, the pre-selected temperature is equal to 300° C.

In some embodiments of the thermal conversion process, the pre-selected temperature is greater than 300° C.

In some embodiments of the thermal conversion process, the pre-selected temperature is equal to 350° C.

In some embodiments of the thermal conversion process, the pre-selected temperature is greater than 350° C.

In some embodiments of the thermal conversion process, the pre-selected temperature is equal to 400° C.

In some embodiments of the thermal conversion process, the pre-selected temperature is greater than 400° C.

In some embodiments of the thermal conversion process, the pre-selected temperature is equal to 450° C.

In some embodiments of the thermal conversion process, the pre-selected temperature is greater than 450° C.

In some embodiments of the thermal conversion process, one or more of the pre-selected time intervals is 2 minutes.

In some embodiments of the thermal conversion process, one or more of the pre-selected time intervals is 5 minutes.

In some embodiments of the thermal conversion process, one or more of the pre-selected time intervals is 10 minutes.

In some embodiments of the thermal conversion process, one or more of the pre-selected time intervals is 15 minutes.

In some embodiments of the thermal conversion process, one or more of the pre-selected time intervals is 20 minutes.

In some embodiments of the thermal conversion process, one or more of the pre-selected time intervals is 25 minutes.

In some embodiments of the thermal conversion process, one or more of the pre-selected time intervals is 30 minutes.

In some embodiments of the thermal conversion process, one or more of the pre-selected time intervals is 35 minutes.

In some embodiments of the thermal conversion process, one or more of the pre-selected time intervals is 40 minutes.

In some embodiments of the thermal conversion process, one or more of the pre-selected time intervals is 45 minutes.

In some of the thermal conversion process, one or more of the pre-selected time intervals is 50 minutes.

In some embodiments of the thermal conversion process, one or more of the pre-selected time intervals is 55 minutes.

In some embodiments of the thermal conversion process, one or more of the pre-selected time intervals is 60 minutes.

In some embodiments of the thermal conversion process, one or more of the pre-selected time intervals is greater than 60 minutes.

In some embodiments of the thermal conversion process, one or more of the pre-selected time intervals is between 2 minutes and 60 minutes.

In some embodiments of the thermal conversion process, one or more of the pre-selected time intervals is between 2 minutes and 90 minutes.

In some embodiments of the thermal conversion process, one or more of the pre-selected time intervals is between 2 minutes and 120 minutes.

In some embodiments of the thermal conversion process, the method for preparing a polyimide film comprises the following steps in order: coating the above-described polyamic acid solution onto a matrix; soft-baking the coated matrix; treating the soft-baked coated matrix at a plurality of pre-selected temperatures for a plurality of pre-selected time intervals whereby the polyimide film exhibits properties that are satisfactory for use in electronics applications like those disclosed herein.

In some embodiments of the thermal conversion process, the method for preparing a polyimide film consists of the following steps in order: coating the above-described polyamic acid solution onto a matrix; soft-baking the coated matrix; treating the soft-baked coated matrix at a plurality of pre-selected temperatures for a plurality of pre-selected time intervals whereby the polyimide film exhibits properties that are satisfactory for use in electronics applications like those disclosed herein.

In some embodiments of the thermal conversion process, the method for preparing a polyimide film consists essentially of the following steps in order: coating the above-described polyamic acid solution onto a matrix; soft-baking the coated matrix; treating the soft-baked coated matrix at a plurality of pre-selected temperatures for a plurality of pre-selected time intervals whereby the polyimide film exhibits properties that are satisfactory for use in electronics applications like those disclosed herein.

Typically, the polyamic acid solutions/polyimides disclosed herein are coated/cured onto a supporting glass substrate to facilitate the processing through the rest of the display making process. At some point in the process as determined by the display maker, the polyimide coating is removed from the supporting glass substrate by a mechanical or laser lift off process. These processes separate the polyimide as a film with the deposited display layers from the glass and enable a flexible format. Often, this polyimide film with deposition layers is then bonded to a thicker, but still flexible, plastic film to provide support for subsequent fabrication of the display.

There are also provided modified-thermal conversion processes wherein conversion catalysts generally cause imidization reactions to run at lower temperatures than would be possible in the absence of such conversion catalysts.

In some embodiments, the polyamic acid solution is converted into a polyimide film via a modified-thermal conversion process.

In some embodiments of the modified-thermal conversion process, the polyamic acid solution further contains conversion catalysts.

In some embodiments of the modified-thermal conversion process, the polyamic acid solution further contains conversion catalysts selected from the group consisting of tertiary amines.

In some embodiments of the modified-thermal conversion process, the polyamic acid solution further contains conversion catalysts selected from the group consisting of tributylamine, dimethylethanolamine, isoquinoline, 1,2-dimethylimidazole, N-methylimidazole, 2-methylimidazole, 2-ethyl-4-imidazole, 3,5-dimethylpyridine, 3,4-dimethylpyridine, 2,5-dimethylpyridine, 5-methylbenzimidazole, and the like.

In some embodiments of the modified-thermal conversion process, the conversion catalyst is present at 5 weight percent or less of the polyamic acid solution.

In some embodiments of the modified-thermal conversion process, the conversion catalyst is present at 3 weight percent or less of the polyamic acid solution.

In some embodiments of the modified-thermal conversion process, the conversion catalyst is present at 1 weight percent or less of the polyamic acid solution.

In some embodiments of the modified-thermal conversion process, the conversion catalyst is present at 1 weight percent of the polyamic acid solution.

In some embodiments of the modified-thermal conversion process, the polyamic acid solution further contains tributylamine as a conversion catalyst.

In some embodiments of the modified-thermal conversion process, the polyamic acid solution further contains dimethylethanolamine as a conversion catalyst.

In some embodiments of the modified-thermal conversion process, the polyamic acid solution further contains isoquinoline as a conversion catalyst.

In some embodiments of the modified-thermal conversion process, the polyamic acid solution further contains 1,2-dimethylimidazole as a conversion catalyst.

In some embodiments of the modified-thermal conversion process, the polyamic acid solution further contains 3,5-dimethylpyridine as a conversion catalyst.

In some embodiments of the modified-thermal conversion process, the polyamic acid solution further contains 5-methylbenzimidazole as a conversion catalyst.

In some embodiments of the modified-thermal conversion process, the polyamic acid solution further contains N-methylimidazole as a conversion catalyst.

In some embodiments of the modified-thermal conversion process, the polyamic acid solution further contains 2-methylimidazole as a conversion catalyst.

In some embodiments of the modified-thermal conversion process, the polyamic acid solution further contains 2-ethyl-4-imidazole as a conversion catalyst.

In some embodiments of the modified-thermal conversion process, the polyamic acid solution further contains 3,4-dimethylpyridine as a conversion catalyst.

In some embodiments of the modified-thermal conversion process, the polyamic acid solution further contains 2,5-dimethylpyridine as a conversion catalyst.

In some embodiments of the modified-thermal conversion process, the polyamic acid solution is coated onto the matrix such that the soft-baked thickness of the resulting film is less than 50 μm.

In some embodiments of the modified-thermal conversion process, the polyamic acid solution is coated onto the matrix such that the soft-baked thickness of the resulting film is less than 40 μm.

In some embodiments of the modified-thermal conversion process, the polyamic acid solution is coated onto the matrix such that the soft-baked thickness of the resulting film is less than 30 μm.

In some embodiments of the modified-thermal conversion process, the polyamic acid solution is coated onto the matrix such that the soft-baked thickness of the resulting film is less than 20 μm.

In some embodiments of the modified-thermal conversion process, the polyamic acid solution is coated onto the matrix such that the soft-baked thickness of the resulting film is between 10 μm and 20 μm.

In some embodiments of the modified-thermal conversion process, the polyamic acid solution is coated onto the matrix such that the soft-baked thickness of the resulting film is between 15 μm and 20 μm.

In some embodiments of the modified-thermal conversion process, the polyamic acid solution is coated onto the matrix such that the soft-baked thickness of the resulting film is 18 μm.

In some embodiments of the modified-thermal conversion process, the polyamic acid solution is coated onto the matrix such that the soft-baked thickness of the resulting film is less than 10 μm.

In some embodiments of the modified-thermal conversion process, the coated matrix is soft baked on a hot plate in proximity mode wherein nitrogen gas is used to hold the coated matrix just above the hot plate.

In some embodiments of the modified-thermal conversion process, the coated matrix is soft baked on a hot plate in full-contact mode wherein the coated matrix is in direct contact with the hot plate surface.

In some embodiments of the modified-thermal conversion process, the coated matrix is soft baked on a hot plate using a combination of proximity and full-contact modes.

In some embodiments of the modified-thermal conversion process, the coated matrix is soft-baked using a hot plate set at 80° C.

In some embodiments of the modified-thermal conversion process, the coated matrix is soft-baked using a hot plate set at 90° C.

In some embodiments of the modified-thermal conversion process, the coated matrix is soft-baked using a hot plate set at 100° C.

In some embodiments of the modified-thermal conversion process, the coated matrix is soft-baked using a hot plate set at 110° C.

In some embodiments of the modified-thermal conversion process, the coated matrix is soft-baked using a hot plate set at 120° C.

In some embodiments of the modified-thermal conversion process, the coated matrix is soft-baked using a hot plate set at 130° C.

In some embodiments of the modified-thermal conversion process, the coated matrix is soft-baked using a hot plate set at 140° C.

In some embodiments of the modified-thermal conversion process, the coated matrix is soft-baked for a total time of more than 10 minutes.

In some embodiments of the modified-thermal conversion process, the coated matrix is soft-baked for a total time of less than 10 minutes.

In some embodiments of the modified-thermal conversion process, the coated matrix is soft-baked for a total time of less than 8 minutes.

In some embodiments of the modified-thermal conversion process, the coated matrix is soft-baked for a total time of less than 6 minutes.

In some embodiments of the modified-thermal conversion process, the coated matrix is soft-baked for a total time of 4 minutes.

In some embodiments of the modified-thermal conversion process, the coated matrix is soft-baked for a total time of less than 4 minutes.

In some embodiments of the modified-thermal conversion process, the coated matrix is soft-baked for a total time of less than 2 minutes.

In some embodiments of the modified-thermal conversion process, the soft-baked coated matrix is subsequently cured at 2 pre-selected temperatures for 2 pre-selected time intervals, the latter of which may be the same or different.

In some embodiments of the modified-thermal conversion process, the soft-baked coated matrix is subsequently cured at 3 pre-selected temperatures for 3 pre-selected time intervals, each of which of the latter of which may be the same or different.

In some embodiments of the modified-thermal conversion process, the soft-baked coated matrix is subsequently cured at 4 pre-selected temperatures for 4 pre-selected time intervals, each of which of the latter of which may be the same or different.

In some embodiments of the modified-thermal conversion process, the soft-baked coated matrix is subsequently cured at 5 pre-selected temperatures for 5 pre-selected time intervals, each of which of the latter of which may be the same or different.

In some embodiments of the modified-thermal conversion process, the soft-baked coated matrix is subsequently cured at 6 pre-selected temperatures for 6 pre-selected time intervals, each of which of the latter of which may be the same or different.

In some embodiments of the modified-thermal conversion process, the soft-baked coated matrix is subsequently cured at 7 pre-selected temperatures for 7 pre-selected time intervals, each of which of the latter of which may be the same or different.

In some embodiments of the modified-thermal conversion process the soft-baked coated matrix is subsequently cured at 8 pre-selected temperatures for 8 pre-selected time intervals, each of which of the latter of which may be the same or different.

In some embodiments of the modified-thermal conversion process, the soft-baked coated matrix is subsequently cured at 9 pre-selected temperatures for 9 pre-selected time intervals, each of which of the latter of which may be the same or different.

In some embodiments of the modified-thermal conversion process, the soft-baked coated matrix is subsequently cured at 10 pre-selected temperatures for 10 pre-selected time intervals, each of which of the latter of which may be the same or different.

In some embodiments of the modified-thermal conversion process, the pre-selected temperature is greater than 80° C.

In some embodiments of the modified-thermal conversion process, the pre-selected temperature is equal to 100° C.

In some embodiments of the modified-thermal conversion process, the pre-selected temperature is greater than 100° C.

In some embodiments of the modified-thermal conversion process, the pre-selected temperature is equal to 150° C.

In some embodiments of the modified-thermal conversion process, the pre-selected temperature is greater than 150° C.

In some embodiments of the modified-thermal conversion process, the pre-selected temperature is equal to 200° C.

In some embodiments of the modified-thermal conversion process, the pre-selected temperature is greater than 200° C.

In some embodiments of the modified-thermal conversion process, the pre-selected temperature is equal to 220° C.

In some embodiments of the modified-thermal conversion process, the pre-selected temperature is greater than 220° C.

In some embodiments of the modified-thermal conversion process, the pre-selected temperature is equal to 230° C.

In some embodiments of the modified-thermal conversion process, the pre-selected temperature is greater than 230° C.

In some embodiments of the modified-thermal conversion process, the pre-selected temperature is equal to 240° C.

In some embodiments of the modified-thermal conversion process, the pre-selected temperature is greater than 240° C.

In some embodiments of the modified-thermal conversion process, the pre-selected temperature is equal to 250° C.

In some embodiments of the modified-thermal conversion process, the pre-selected temperature is greater than 250° C.

In some embodiments of the modified-thermal conversion process, the pre-selected temperature is equal to 260° C.

In some embodiments of the modified-thermal conversion process, the pre-selected temperature is greater than 260° C.

In some embodiments of the modified-thermal conversion process, the pre-selected temperature is equal to 270° C.

In some embodiments of the modified-thermal conversion process, the pre-selected temperature is greater than 270° C.

In some embodiments of the modified-thermal conversion process, the pre-selected temperature is equal to 280° C.

In some embodiments of the modified-thermal conversion process, the pre-selected temperature is greater than 280° C.

In some embodiments of the modified-thermal conversion process, the pre-selected temperature is equal to 290° C.

In some embodiments of the modified-thermal conversion process, the pre-selected temperature is greater than 290° C.

In some embodiments of the modified-thermal conversion process, the pre-selected temperature is equal to 300° C.

In some embodiments of the modified-thermal conversion process, the pre-selected temperature is less than 300° C.

In some embodiments of the modified-thermal conversion process, the pre-selected temperature is less than 290° C.

In some embodiments of the modified-thermal conversion process, the pre-selected temperature is less than 280° C.

In some embodiments of the modified-thermal conversion process, the pre-selected temperature is less than 270° C.

In some embodiments of the modified-thermal conversion process, the pre-selected temperature is less than 260° C.

In some embodiments of the modified-thermal conversion process, the pre-selected temperature is less than 250° C.

In some embodiments of the modified-thermal conversion process, one or more of the pre-selected time intervals is 2 minutes.

In some embodiments of the modified-thermal conversion process, one or more of the pre-selected time intervals is 5 minutes.

In some embodiments of the modified-thermal conversion process, one or more of the pre-selected time intervals is 10 minutes.

In some embodiments of the modified-conversion process, one or more of the pre-selected time intervals is 15 minutes.

In some embodiments of the modified-thermal conversion process, one or more of the pre-selected time intervals is 20 minutes.

In some embodiments of the modified-thermal conversion process, one or more of the pre-selected time intervals is 25 minutes.

In some embodiments of the modified-thermal conversion process, one or more of the pre-selected time intervals is 30 minutes.

In some embodiments of the modified-thermal conversion process, one or more of the pre-selected time intervals is 35 minutes.

In some embodiments of the modified-thermal conversion process, one or more of the pre-selected time intervals is 40 minutes.

In some embodiments of the modified-thermal conversion process, one or more of the pre-selected time intervals is 45 minutes.

In some embodiments of the modified-thermal conversion process, one or more of the pre-selected time intervals is 50 minutes.

In some embodiments of the modified-thermal conversion process, one or more of the pre-selected time intervals is 55 minutes.

In some embodiments of the modified-thermal conversion process, one or more of the pre-selected time intervals is 60 minutes.

In some embodiments of the modified-thermal conversion process, one or more of the pre-selected time intervals is greater than 60 minutes.

In some embodiments of the modified-thermal conversion process, one or more of the pre-selected time intervals is between 2 minutes and 60 minutes.

In some embodiments of the modified-thermal conversion process, one or more of the pre-selected time intervals is between 2 minutes and 90 minutes.

In some embodiments of the modified-thermal conversion process, one or more of the pre-selected time intervals is between 2 minutes and 120 minutes.

In some embodiments of the modified-thermal conversion process, the method for preparing a polyimide film comprises the following steps in order: coating the above-described polyamic acid solution including a conversion chemical onto a matrix; soft-baking the coated matrix; treating the soft-baked coated matrix at a plurality of pre-selected temperatures for a plurality of pre-selected time intervals whereby the polyimide film exhibits properties that are satisfactory for use in electronics applications like those disclosed herein.

In some embodiments of the modified-thermal conversion process, the method for preparing a polyimide film consists of the following steps in order: coating the above-described polyamic acid solution including a conversion chemical onto a matrix; soft-baking the coated matrix; treating the soft-baked coated matrix at a plurality of pre-selected temperatures for a plurality of pre-selected time intervals whereby the polyimide film exhibits properties that are satisfactory for use in electronics applications like those disclosed herein.

In some embodiments of the modified-thermal conversion process, the method for preparing a polyimide film consists essentially of the following steps in order: coating the above-described polyamic acid solution including a conversion chemical onto a matrix; soft-baking the coated matrix; treating the soft-baked coated matrix at a plurality of pre-selected temperatures for a plurality of pre-selected time intervals whereby the polyimide film exhibits properties that are satisfactory for use in electronics applications like those disclosed herein.

6. The Electronic Device

The polyimide films disclosed herein can be suitable for use in a number of layers in electronic display devices such as OLED and LCD Displays. Nonlimiting examples of such layers include device substrates, touch panels, substrates for color filter sheets, cover films, and others. The particular materials' properties requirements for each application are unique and may be addressed by appropriate composition(s) and processing condition(s) for the polyimide films disclosed herein.

In some embodiments, the flexible replacement for glass in an electronic device is a polyimide film comprising a polyimide having the repeat unit of Formula III, as described in detail above.

In some embodiments, there is provided an organic electronic device having at least one layer comprising a polyimide film having a repeat unit of Formula III, as described in detail above.

Organic electronic devices that may benefit from having one or more layers including at least one compound as described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), (4) devices that convert light of one wavelength to light of a longer wavelength, (e.g., a down-converting phosphor device); and (5) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

Figure 2:
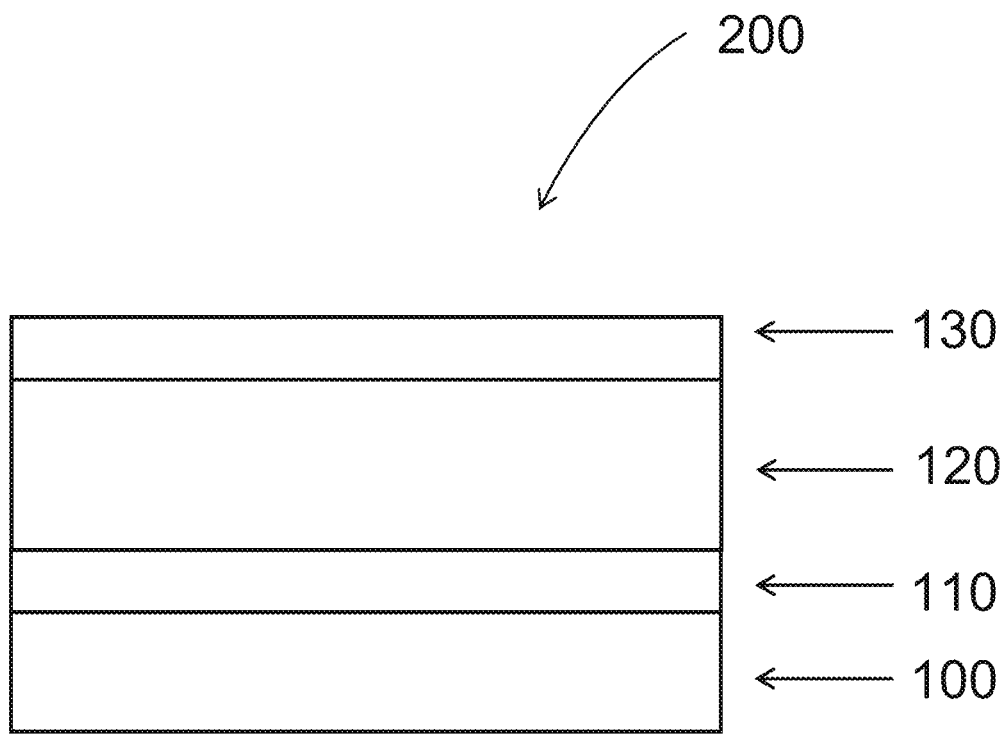
FIG. 2 includes an illustration of one example of an electronic device that includes a flexible replacement for glass.

One illustration of a polyimide film that can act as a flexible replacement for glass as described herein is shown in FIG. 1. The flexible film 100 can have the properties as described in the embodiments of this disclosure. In some embodiments, the polyimide film that can act as a flexible replacement for glass is included in an electronic device. FIG. 2 illustrates the case when the electronic device 200 is an organic electronic device. The device 200 has a substrate 100, an anode layer 110 and a second electrical contact layer, a cathode layer 130, and a photoactive layer 120 between them. Additional layers may optionally be present. Adjacent to the anode may be a hole injection layer (not shown), sometimes referred to as a buffer layer. Adjacent to the hole injection layer may be a hole transport layer (not shown), including hole transport material. Adjacent to the cathode may be an electron transport layer (not shown), including an electron transport material. As an option, devices may use one or more additional hole injection or hole transport layers (not shown) next to the anode 110 and/or one or more additional electron injection or electron transport layers (not shown) next to the cathode 130. Layers between 110 and 130 are individually and collectively referred to as the organic active layers. Additional layers that may or may not be present include color filters, touch panels, and/or cover sheets. One or more of these layers, in addition to the substrate 100, may also be made from the polyimide films disclosed herein.

The different layers will be discussed further herein with reference to FIG. 2. However, the discussion applies to other configurations as well.

In some embodiments, the different layers have the following range of thicknesses: substrate 100, 5-100 microns, anode 110, 500-5000 Å, in some embodiments, 1000-2000 Å; hole injection layer (not shown), 50-2000 Å, in some embodiments, 200-1000 Å; hole transport layer (not shown), 50-3000 Å, in some embodiments, 200-2000 Å; photoactive layer 120, 10-2000 Å, in some embodiments, 100-1000 Å; electron transport layer (not shown), 50-2000 Å, in some embodiments, 100-1000 Å; cathode 130, 200-10000 Å, in some embodiments, 300-5000 Å. The desired ratio of layer thicknesses will depend on the exact nature of the materials used.

In some embodiments, the organic electronic device (OLED) contains a flexible replacement for glass as disclosed herein.

In some embodiments, there is provided an organic electronic device, wherein the device substrate comprises the polyimide film disclosed herein. In some embodiments, the device is an organic light emitting diode (OLED).

In some embodiments, an organic electronic device includes a substrate, an anode, a cathode, and a photoactive layer therebetween, and further includes one or more additional organic active layers. In some embodiments, the additional organic active layer is a hole transport layer. In some embodiments, the additional organic active layer is an electron transport layer. In some embodiments, the additional organic layers are both hole transport and electron transport layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also include an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

Optional hole injection layers can include hole injection materials. The term "hole injection layer" or "hole injection material" is intended to mean electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules, and may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propane-sulfonic acid), and the like. The hole injection layer 120 can include charge transfer compounds, and the like, such as copper phthalocyanine and the tetrathiafulvalene-tetracyanoquinodimethane system (TTF-TCNQ). In some embodiments, the hole injection layer 120 is made from a dispersion of a conducting polymer and a colloid-forming polymeric acid. Such materials have been described in, for example, published U.S. patent applications 2004-0102577, 2004-0127637, and 2005-0205860.

Other layers can include hole transport materials. Examples of hole transport materials for the hole transport layer have been summarized for example, in Kirk-Othmer Encyclopedia of Chemical Technology, Fourth Edition, Vol. 18, p. 837-860, 1996, by Y. Wang. Both hole transporting small molecules and polymers can be used. Commonly used hole transporting molecules include, but are not limited to: 4,4',4"-tris(N,N-diphenyl-amino)-triphenylamine (TDATA); 4,4',4"-tris(N-3-methylphenyl-N-phenyl-amino)-triphenylamine (MTDATA); N,N'-diphenyl-N,N'-bis(3-methylphenyl)-[1,1'-biphenyl]-4,4'-diamine (TPD); 4,4'-bis(carbazol-9-yl)biphenyl (CBP); 1,3-bis(carbazol-9-yl)benzene (mCP); 1,1-bis[(di-4-tolylamino) phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA), α-phenyl-4-N, N-diphenylaminostyrene (TPS); p-(diethylamino)benzaldehyde diphenylhydrazone (DEH); triphenylamine (TPA); bis[4-(N,N-diethylamino)-2-methylphenyl](4-methylphenyl)methane (MPMP); 1-phenyl-3-[p-(diethylamino)styryl]-5-[p-(diethylamino)phenyl] pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); N,N'-bis(naphthalen-1-yl)-N,N'-bis-(phenyl)benzidine (α-NPB); and porphyrinic compounds, such as copper phthalocyanine. Commonly used hole transporting polymers include, but are not limited to, polyvinylcarbazole, (phenylmethyl)polysilane, poly(dioxythiophenes), polyanilines, and polypyrroles. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

Depending upon the application of the device, the photoactive layer 120 can be a light-emitting layer that is activated by an applied voltage (such as in a light-emitting diode or light-emitting electrochemical cell), a layer of material that absorbs light and emits light having a longer wavelength (such as in a down-converting phosphor device), or a layer of material that responds to radiant energy and generates a signal with or without an applied bias voltage (such as in a photodetector or photovoltaic device).

In some embodiments, the photoactive layer includes a compound comprising an emissive compound having as a photoactive material. In some embodiments, the photoactive layer further comprises a host material. Examples of host materials include, but are not limited to, chrysenes, phenanthrenes, triphenylenes, phenanthrolines, naphthalenes, anthracenes, quinolines, isoquinolines, quinoxalines, phenylpyridines, carbazoles, indolocarbazoles, furans, benzofurans, dibenzofurans, benzodifurans, and metal quinolinate complexes. In some embodiments, the host materials are deuterated.

In some embodiments, the photoactive layer comprises (a) a dopant capable of electroluminescence having an emission maximum between 380 and 750 nm, (b) a first host compound, and (c) a second host compound. Suitable second host compounds are described above.

In some embodiments, the photoactive layer includes only (a) a dopant capable of electroluminescence having an emission maximum between 380 and 750 nm, (b) a first host compound, and (c) a second host compound, where additional materials that would materially alter the principle of operation or the distinguishing characteristics of the layer are not present.

In some embodiments, the first host is present in higher concentration than the second host, based on weight in the photoactive layer.

In some embodiments, the weight ratio of first host to second host in the photoactive layer is in the range of 10:1 to 1:10. In some embodiments, the weight ratio is in the range of 6:1 to 1:6; in some embodiments, 5:1 to 1:2; in some embodiments, 3:1 to 1:1.

In some embodiments, the weight ratio of dopant to the total host is in the range of 1:99 to 20:80; in some embodiments, 5:95 to 15:85.

In some embodiments, the photoactive layer comprises (a) a red light-emitting dopant, (b) a first host compound, and (c) a second host compound.

In some embodiments, the photoactive layer comprises (a) a green light-emitting dopant, (b) a first host compound, and (c) a second host compound.

In some embodiments, the photoactive layer comprises (a) a yellow light-emitting dopant, (b) a first host compound, and (c) a second host compound.

Optional layers can function both to facilitate electron transport, and also serve as a confinement layer to prevent quenching of the exciton at layer interfaces. Preferably, this layer promotes electron mobility and reduces exciton quenching.

In some embodiments, such layers include other electron transport materials. Examples of electron transport materials which can be used in the optional electron transport layer, include metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato) hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); triazines; fullerenes; and mixtures thereof. In some embodiments, the electron transport material is selected from the group consisting of metal quinolates and phenanthroline derivatives. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$, Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

An optional electron injection layer may be deposited over the electron transport layer. Examples of electron injection materials include, but are not limited to, Li-containing organometallic compounds, LiF, $Li_2O$, Li quinolate, Cs-containing organometallic compounds, CsF, $Cs_2O$, and $Cs_2CO_3$. This layer may react with the underlying electron transport layer, the overlying cathode, or both. When an electron injection layer is present, the amount of material deposited is generally in the range of 1-100 Å, in some embodiments 1-10 Å.

The cathode 130 is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

It is known to have other layers in organic electronic devices. For example, there can be layers (not shown) between the anode 110 and hole injection layer (not shown) to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layer 120, or cathode layer 130, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device layers can generally be formed by any deposition technique, or combinations of techniques, including vapor deposition, liquid deposition, and thermal transfer. Substrates such as glass, plastics, and metals can be used. Conventional vapor deposition techniques can be used, such as thermal evaporation, chemical vapor deposition, and the like. The organic layers can be applied from solutions or dispersions in suitable solvents, using conventional coating or printing techniques, including but not limited to coating, dip-coating, roll-to-roll techniques, ink-jet printing, continuous nozzle printing, screen-printing, gravure printing and the like.

For liquid deposition methods, a suitable solvent for a particular compound or related class of compounds can be readily determined by one skilled in the art. For some applications, it is desirable that the compounds be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes or aromatics such as toluene, xylenes, trifluorotoluene and the like. Other suitable liquids for use in making the liquid composition, either as a solution or dispersion as described herein, including the new compounds, includes, but not limited to, chlorinated hydrocarbons (such as methylene chloride, chloroform, chlorobenzene), aromatic hydrocarbons (such as substituted and non-substituted toluenes and xylenes), including triflurotoluene), polar solvents (such as tetrahydrofuran (THP), N-methyl pyrrolidone) esters (such as ethylacetate) alcohols (isopropanol), ketones (cyclopentatone) and mixtures thereof. Suitable solvents for electroluminescent materials have been described in, for example, published PCT application WO 2007/145979.

In some embodiments, the device is fabricated by liquid deposition of the hole injection layer, the hole transport layer, and the photoactive layer, and by vapor deposition of the anode, the electron transport layer, an electron injection layer and the cathode onto the flexible substrate.

It is understood that the efficiency of devices can be improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

In some embodiments, the device has the following structure, in order: substrate, anode, hole injection layer, hole transport layer, photoactive layer, electron transport layer, electron injection layer, cathode.

Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further illustrated in the following examples, which do not limit the scope of the invention described in the claims.

Synthesis Example 1

This example illustrates how a compound having Formula I could be prepared, Compound 1.

Step 1:

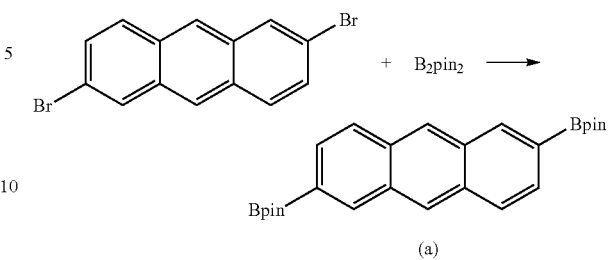

A Miyaura borylation reaction can be used to form (a). 2,6-dibromoanthracene can be reacted with bis(pinacolato)diboron in the presence of KOAc and $PdCl_2(dppf)$ catalyst in a solvent such as dioxane or DMSO at a temperature of 80° C. The product (a) can be isolated by conventional techniques.

Step 2:

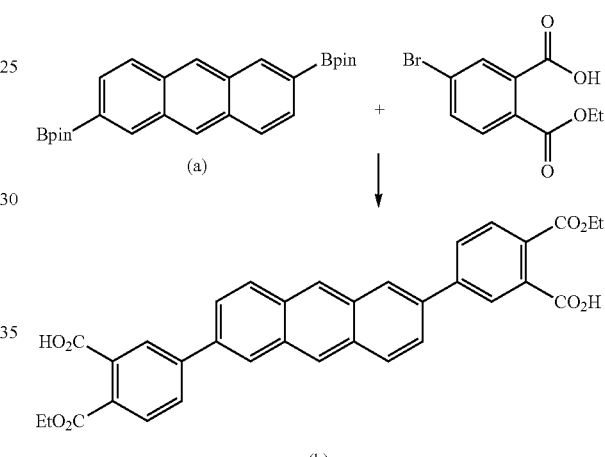

Product (a) can be reacted with the monoethyl ester of 4-bromophthalic acid in the presence of base and $Pd(PPh_3)_4$ catalyst in a toluene/ethanol/water solvent. The product (b) can be isolated by conventional techniques. Alternatively, the dimethyl ester of 4-bromophthalic acid can be reacted with product (a) to generate the corresponding tetraester. The tetraester can be reacted in Step 3 below, in place of product (b).

Step 3:

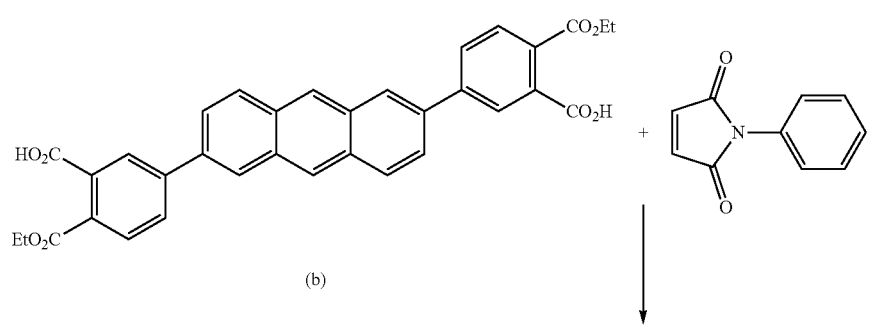

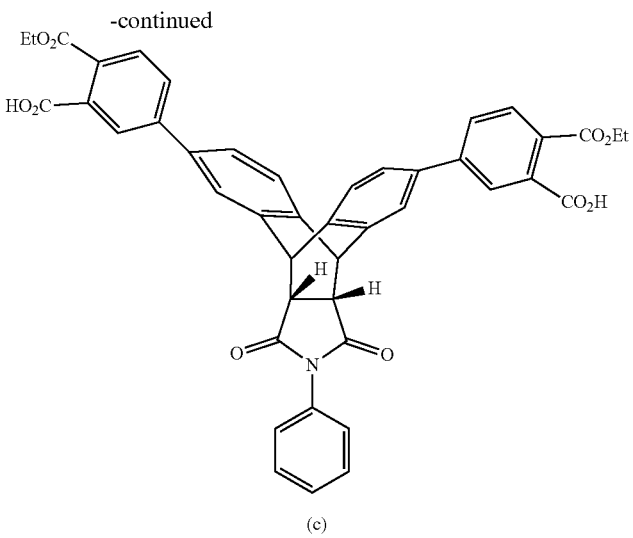

(c)

A mixture of product (b) and N-phenylmaleimide can be heated at 150° C. for 1-2 hours under nitrogen atmosphere in 1,2-dichloroethane solvent. The product (c) can be isolated by conventional techniques.

Step 4:

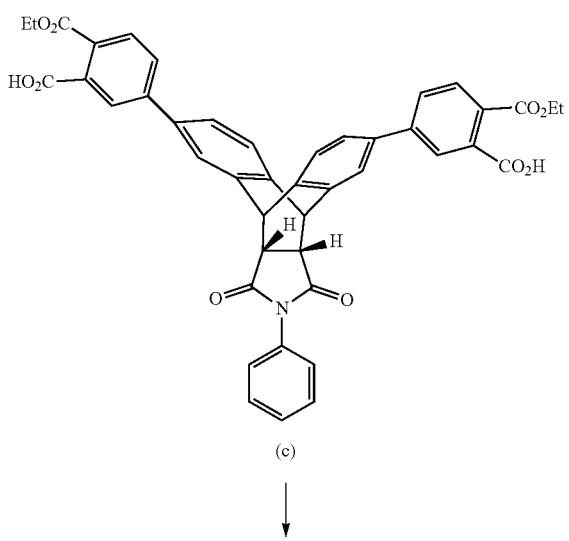

(c)

↓

-continued

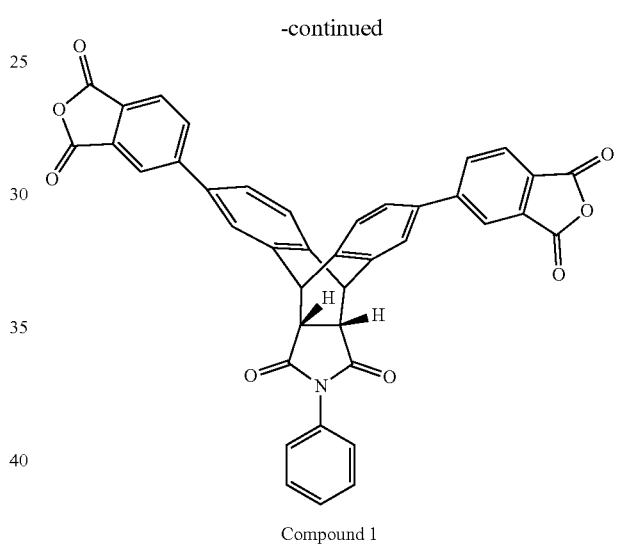

Compound 1

Product (c) can be reacted with thionyl chloride in chloroform under nitrogen with heating to 70-70° C. The intermediate reaction product can be isolated and further treated with acetic anhydride with heating to 90-95° C. The product, Compound 1, can be isolated by filtration and vacuum drying.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A polyanhydride having Formula I

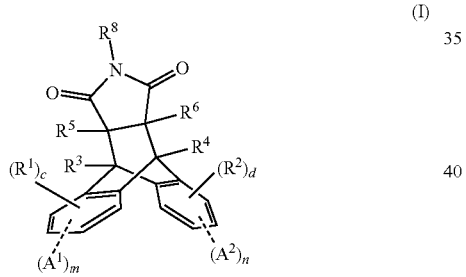

(I)

wherein:
- $R^1$ and $R^2$ are the same or different at each occurrence and are selected from the group consisting of F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy;
- $R^3$ is selected from the group consisting of $A^3$, H, F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy;
- $R^4$ is selected from the group consisting of $A^4$, H, F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy;
- $R^5$ and $R^6$ are the same or different and are selected from the group consisting of H, F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy;
- $R^8$ is selected from the group consisting of alkyl, silyl, unsubstituted or substituted hydrocarbon aryl, and unsubstituted or substituted heteroaryl;
- c and d are the same or different and are an integer from 0 to the maximum available;
- m and n are the same or different and are 0 or 1;
- $A^1$ to $A^4$ are the same or different and have the formula

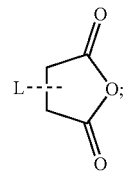

- L is the same or different at each occurrence and is a bond or a hydrocarbon aryl; and
- single dashed lines between two rings indicate that the rings are joined by a single bond or fused together at any available position;
- with the proviso that at least two of $A^1$ to $A^4$ are present.

2. The polyanhydride of claim 1, having Formula IA

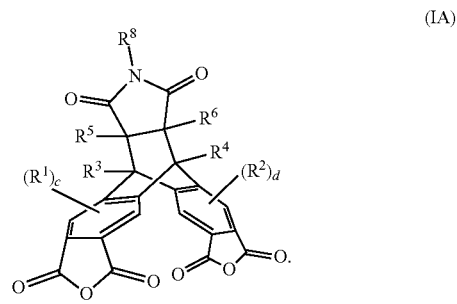

(IA)

3. The polyanhydride of claim 2, wherein
$R^3$ and $R^4$ are the same or different and are selected from the group consisting of H, F, CN, alkyl, fluoroalkyl, alkoxy, fluoroalkoxy, silyl, siloxy, unsubstituted or substituted hydrocarbon aryl, unsubstituted or substituted heteroaryl, and unsubstituted or substituted aryloxy.

4. A polyamic acid which is the reaction product of one or more polyanhydrides with one or more polyamines, wherein 10-100 mol % of the one or more polyanhydrides are polyanhydrides having Formula I, according to claim 1.

5. A polyamic acid having a repeat unit of Formula II

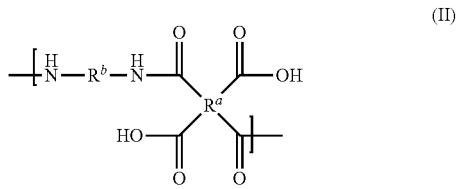

(II)

where:
- $R^a$ is the same or different at each occurrence and represents one or more tetracarboxylic acid component residues; and
- $R^b$ is the same or different at each occurrence and represents one or more aromatic diamine residues;

wherein 10-100 mol % of $R^a$ is a dianhydride residue from one or more dianhydrides having Formula I, according to claim 1.

6. A liquid composition comprising (a) the polyamic acid according to claim 4, and (b) a high-boiling, aprotic solvent.

7. A polyimide formed by imidization of the polyamic acid according to claim 4.

8. A polyimide having a repeat unit of Formula III

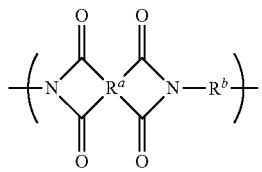

(III)

where:

$R^a$ is the same or different at each occurrence and represents one or more tetracarboxylic acid component residues; and $R^b$ is the same or different at each occurrence and represents one or more aromatic diamine residues;

wherein 10-100 mol % of $R^a$ is a dianhydride residue from one or more dianhydrides having Formula I.

9. An organic electronic device having at least one layer comprising a polyimide film having a repeat unit of Formula III, according to claim 8.

10. The electronic device according to claim 9, wherein the layer is used in device components selected from the group consisting of device substrates, substrates for color filter sheets, cover films, and touch screen panels.

* * * * *